United States Patent [19]

Kamibayashi et al.

[11] 4,419,518
[45] Dec. 6, 1983

[54] 1,4-DIHYDROPYRIDINE DERIVATIVES

[75] Inventors: Masato Kamibayashi, Hasuda; Shinji Tsuchiya, Washimiya; Kozo Hiratsuka, Tsurugashima, all of Japan

[73] Assignee: Tokyo Tanabe Co. L.T.D., Japan

[21] Appl. No.: 402,124

[22] Filed: Jul. 26, 1982

[51] Int. Cl.$^3$ .................................. C07D 401/12
[52] U.S. Cl. ................................ 546/279; 424/266
[58] Field of Search .................................. 546/279

[56] References Cited

U.S. PATENT DOCUMENTS

| 3,905,970 | 9/1975 | Bossert et al. | 424/256 |
| 3,946,027 | 3/1976 | Bossert et al. | 546/256 |
| 4,146,627 | 3/1979 | Wehinger | 546/279 |
| 4,380,547 | 4/1983 | Materne | 546/279 |

FOREIGN PATENT DOCUMENTS 140989 11/1981 Japan .................................. 546/256

Primary Examiner—Jane T. Fan
Attorney, Agent, or Firm—McGlew and Tuttle

[57] ABSTRACT

New 1,4-dihydropyridine derivatives of the formula [I] are provided:

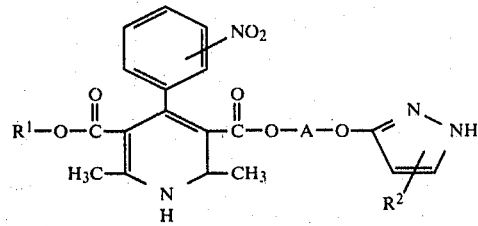

wherein $R^1$ represents a $C_{1-4}$ alkyl group or a $C_{3-6}$ alkoxyalkyl group, $R^2$ represents a $C_{1-8}$ alkyl group, and A represents an unsubstituted hexamethylene group or a substituted hexamethylene group having one or two $C_{1-3}$ alkyl groups. The 1,4-dihydropyridine derivatives have vasodilating and hypotensive activity which is kept for a long period, and are useful in the treatment of cardiovascular disease and hypertention.

11 Claims, No Drawings

1,4-DIHYDROPYRIDINE DERIVATIVES

BACKGROUND OF THE INVENTION (1) Field of the Invention

The present invention relates to novel 1,4-dihydropyridine derivatives of the following general formula [I]:

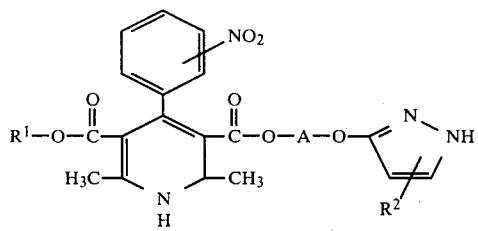

[I]

wherein $R^1$ represents an alkyl group having from 1 to 4 carbon atoms or an alkoxyalkyl group having from 3 to 6 carbon atoms, $R^2$ represents an alkyl group having from 1 to 8 carbon atoms, and A represents a hexamethylene group which may optionally be substituted by one or two alkyl groups having from 1 to 3 carbon atoms, which possess a hypotensive effect.

(2) Description of the Prior Art

Heretofore, there have been known, as 1,4-dihydropyridine derivatives, 4-(2-nitrophenyl)-2,6-dimethyl-1,4-dihydropyridine-3,5-dicarboxylic acid dimethyl ester (U.S. Pat. No. 3,644,627; hereinafter referred to as Nifedipine), 4-(3-nitrophenyl)-2,6-dimethyl-1,4-dihydropyridine-3,5-dicarboxylic acid 3-methyl ester 5-β-(N-benzyl-N-methylamino)ethyl ester hydrochloride (Japanese Patent Publication No. 45075/1980; hereinafter referred to as Nicardipine) etc. which are useful as agents for improving the coronary circulation or the cerebral circulation. However, the vasodilating effect and the hypotensive effect resulting from said effect of these compounds have been reported to disappear within a short period of time, such as 30–40 minutes or so, at the effective intravenous dosage at which they become significant, for example, 10 μg/kg, and also to be accompanied by a phenomenon of an increase in heart rate, which indicates one element to increase the burden on the function of the heart (Arzneimittel-Forschung, Vol. 22, No. 1, p. 33, 1972; ibid., Vol. 26, No. 12, p. 2172, 1976; Toho Igakukai Zasshi, Vol. 26, No. 2, p. 48, 1972). Therefore, when these compounds are to be employed as remedies for hypertention, cardiovascular diseases etc. which require continuous use of drug for a prolonged period of time, the improvement of the preparation, for example, by making it slow-releasing and the like, frequent administration which enhances the manifestation of side effects, or use in combination with other drugs is needed.

SUMMARY OF THE INVENTION

The subject of the present invention is to provide the 1,4-dihydropyridine derivatives of the above general formula [I] which possess a long-lasting hypotensive effect resulting from the vasodilating effect and are of very low ability to change the heart rate and therefore are useful as remedies for hypertention and cardiovascular diseases.

DESCRIPTION OF THE PREFERRED EMBODIMENT

The compounds of the present invention [I] include the tautomers represented by the following formulae:

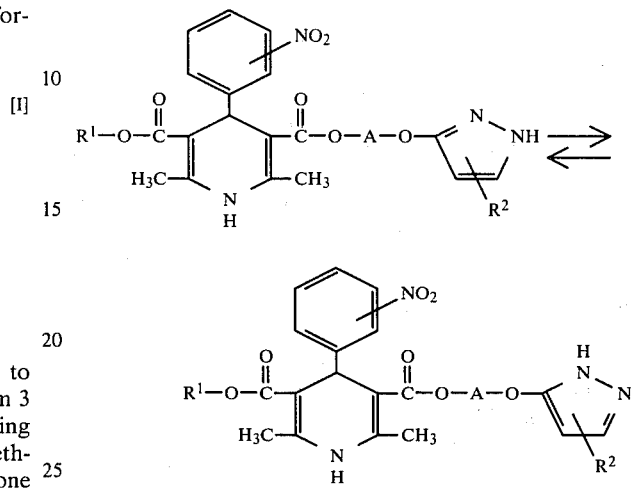

wherein $R^1$, $R^2$ and A are as defined above.

While the nitrophenyl group at the 4-position may include those having the nitro group at the ortho-, meta- or para-position. A tendency to reduce the hypotensive effect was observed in the case of the para-nitrophenyl group.

As the ester (—COOR$^1$) at the 3-position, there may be included alkyl esters such as methyl, ethyl, normalpropyl, isopropyl, isobutyl etc., and alkoxyalkyl esters such as 2-methoxyethyl, 2-ethoxyethyl, 2-normalpropoxyethyl, 2-isopropoxyethyl, 2-isobutoxyethyl, 3-methoxypropyl, 3-ethoxypropyl, 2-methoxypropyl, 1-methyl-2-methoxypropyl, 4-methoxybutyl, 4-ethoxybutyl, 3-methoxybutyl etc. in the case of the alkoxyalkyl esters, 2-alkoxyethyl esters are suitable.

As the alkyl-substituted-3-pyrazolyloxy group

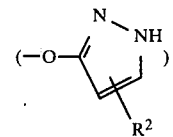

which is one constitutional element of the ester group at the 5-position, there may be included 3-pyrazolyloxy groups which are substituted at the 4- or 5-position by an alkyl group such as methyl, ethyl, normalpropyl, isopropyl, normalbutyl, isobutyl, hexyl, octyl etc. Further, as the other constitutional element, i.e. the hexamethylene group (—A—) which may optionally be substituted by one or two alkyl groups, there may be included hexamethylene group, 1-methylhexamethylene group, 5-methylhexamethylene group, 1, 6-dimethylhexamethylene group, 2,5-dimethylhexamethylene group, 3,4-dimethylhexamethylene group, 5,5-dimethylhexamethylene group, 1,6-diethylhexamethylene group, 3,4-diethylhexamethylene group, 2,2-diethylhexamethylene group, 1,6-diisopropylhexamethylene group, 2,5-diisopropylhexamethylene group etc.

Representative specific examples of the compounds of the present invention [I] are given below.

(Compound 1) 1,4-Dihydro-2,6-dimethyl-4-(3-nitrophenyl)pyridine-3,5-dicarboxylic acid 3-methyl ester 5-[6-(5-methyl-3-pyrazolyloxy)hexyl]ester;

(Compound 2) 1,4-Dihydro-2,6-dimethyl-4-(3-nitrophenyl)pyridine-3,5-dicarboxylic acid 3-methyl ester 5-[6-(5-isopropyl-3-pyrazolyloxy)hexyl]ester;

(Compound 3) 1,4-Dihydro-2,6-dimethyl-4-(3-nitrophenyl)pyridine-3,5-dicarboxylic acid 3-ethyl ester 5-[6-(5-methyl-3-pyrazolyloxy)hexyl]ester;

(Compound 4) 1,4-Dihydro-2,6-dimethyl-4-(3-nitrophenyl)pyridine-3,5-dicarboxylic acid 3-isopropyl ester 5-[6-(5-methyl-3-pyrazolyloxy)hexyl]ester;

(Compound 5) 1,4-Dihydro-2,6-dimethyl-4-(3-nitrophenyl)pyridine-3,5-dicarboxylic acid 3-(2-methoxyethyl) ester 5-[6-(5-methyl-3-pyrazolyloxy)hexyl]ester;

(Compound 6) 1,4-Dihydro-2,6-dimethyl-4-(2-nitrophenyl)pyridine-3,5-dicarboxylic acid 3-methyl ester 5-[6-(5-methyl-3-pyrazolyloxy)hexyl]ester;

(Compound 7) 1,4-Dihydro-2,6-dimethyl-4-(3-nitrophenyl)pyridine-3,5-dicarboxylic acid 3-ethyl ester 5-[6-(5-isopropyl-3-pyrazolyloxy)hexyl]ester;

(Compound 8) 1,4-Dihydro-2,6-dimethyl-4-(3-nitrophenyl)pyridine-3,5-dicarboxylic acid 3-isopropyl ester 5-[6-(5-isopropyl-3-pyrazolyloxy)hexyl]ester;

(Compound 9) 1,4-Dihydro-2,6-dimethyl-4-(3-nitrophenyl)pyridine-3,5-dicarboxylic acid 3-isobutyl ester 5-[6-(5-ethyl-3-pyrazolyloxy)hexyl]ester;

(Compound 10) 1,4-Dihydro-2,6-dimethyl-4-(3-nitrophenyl)pyridine-3,5-dicarboxylic acid 3-(2-normalpropoxyethyl) ester 5-[6-(5-ethyl-3-pyrazolyloxy)hexyl]ester;

(Compound 11) 1,4-Dihydro-2,6-dimethyl-4-(3-nitrophenyl)pyridine-3,5-dicarboxylic acid 3-(2-isobutoxyethyl) ester 5-[6-(5-methyl-3-pyrazolyloxy)hexyl]ester;

(Compound 12) 1,4-Dihydro-2,6-dimethyl-4-(2-nitrophenyl)pyridine-3,5-dicarboxylic acid 3-isopropyl ester 5-[6-(5-normalbutyl-3-pyrazolyloxy)hexyl]ester;

(Compound 13) 1,4-Dihydro-2,6-dimethyl-4-(3-nitrophenyl)pyridine-3,5-dicarboxylic acid 3-methyl ester 5-[6-(5-normalbutyl-3-pyrazolyloxy)hexyl]ester;

(Compound 14) 1,4-Dihydro-2,6-dimethyl-4-(3-nitrophenyl)pyridine-3,5-dicarboxylic acid 3-normalpropyl ester 5-[6-(5-isopropyl-3-pyrazolyloxy)hexyl]ester;

(Compound 15) 1,4-Dihydro-2,6-dimethyl-4-(2-nitrophenyl)pyridine-3,5-dicarboxylic acid 3-methyl ester 5-[6-(5-octyl-3-pyrazolyloxy)hexyl]ester;

(Compound 16) 1,4-Dihydro-2,6-dimethyl-4-(3-nitrophenyl)pyridine-3,5-dicarboxylic acid 3-methyl ester 5-[6-(5-ethyl-3-pyrazolyloxy)hexyl]ester;

(Compound 17) 1,4-Dihydro-2,6-dimethyl-4-(3-nitrophenyl)pyridine-3,5-dicarboxylic acid 3-methyl ester 5-[6-(5-methyl-3-pyrazolyloxy)-1-methylhexyl]ester;

(Compound 18) 1,4-Dihydro-2,6-dimethyl-4-(3-nitrophenyl)pyridine-3,5-dicarboxylic acid 3-methyl ester 5-[6-(5-hexyl-3-pyrazolyloxy)hexyl]ester;

(Compound 19) 1,4-Dihydro-2,6-dimethyl-4-(3-nitrophenyl)pyridine-3,5-dicarboxylic acid 3-(2-isopropoxyethyl) ester 5-[6-(5-methyl-3-pyrazolyloxy)hexyl]ester.

Test examples of the pharmacological activity of the compounds of the present invention [I] are given below.

[Hypotensive Effect]

The hypotensive effect and the duration of said effect of the compounds described above as the specific examples of the compounds of the present invention [I] were tested using adult dogs anesthetized by intravenous administration of 30 mg/kg of sodium pentobarbital.

This test was carried out using groups of 5-6 dogs each and hematologically measuring the blood pressure and the heart rate at the right femoral artery of each dog. The blood pressure and the heart rate were obtained by measuring on a pressure transducer MPU-0.5 (manufactured by Nippon Koden Co.) and a pulse rate tachometer RT-2 (manufactured by Nippon Koden Co.) respectively and recording on a pen oscillograph WI-380 (manufactured by Nippon Koden Co.). Administration of each compound was carried out by injecting each compound dissolved in a 10% polyethylene glycol aqueous solution into the femoral vein. The dosages were established at 3 $\mu$g/kg and 10 $\mu$g/kg. The duration was obtained by measuring the time from when the effect manifested to when it died out, after administration of each compound.

The results are as set forth in Table 1. The heart rate was expressed as the increase or decrease of the heart rate per minute between before and after administration of each compound, and the hypotensive effect was expressed as the difference in mean blood pressure between before and after administration of each compound. The duration was expressed in the unit of minutes. In addition, the heart rate and the hypotensive effect of Nifedipine and Nicardipine measured by the present inventors are also set forth in the same table for comparison.

TABLE 1

| Compound | Dosage $\mu$g/kg i.v. | Heart Rate $\Delta$Heart Rate/ min. $\pm$ S.E. | Hypotensive Effect Mean Blood Pressure $\Delta$mmHg $\pm$ S.E. | Duration min. $\pm$ S.E. |
|---|---|---|---|---|
| Nifedipine | 3 | 5.1 $\pm$ 0.6 | −20.1 $\pm$ 1.4 | 19.0 $\pm$ 1.3 |
|  | 10 | 9.0 $\pm$ 1.2 | −43.0 $\pm$ 3.9 | 40.6 $\pm$ 3.3 |
| Nicardipine | 3 | 19.0 $\pm$ 3.5 | −13.3 $\pm$ 2.5 | 20.1 $\pm$ 5.0 |
|  | 10 | 23.0 $\pm$ 4.5 | −23.5 $\pm$ 2.8 | 32.5 $\pm$ 6.9 |
| Compound 1 | 3 | 0.8 $\pm$ 0.4 | −14.5 $\pm$ 1.3 | 46.5 $\pm$ 2.8 |
|  | 10 | 1.0 $\pm$ 2.6 | −24.3 $\pm$ 1.8 | 103.6 $\pm$ 4.3 |
| Compound 2 | 3 | −1.2 $\pm$ 1.9 | −18.6 $\pm$ 1.2 | 73.5 $\pm$ 5.3 |
|  | 10 | −3.6 $\pm$ 1.0 | −29.1 $\pm$ 2.4 | 180 or longer |
| Compound 3 | 3 | 3.2 $\pm$ 0.8 | −14.9 $\pm$ 1.4 | 53.5 $\pm$ 5.2 |
|  | 10 | 6.1 $\pm$ 3.5 | −27.4 $\pm$ 2.7 | 141.0 $\pm$ 6.7 |
| Compound 4 | 3 | 1.4 $\pm$ 1.7 | −12.5 $\pm$ 2.8 | 43.4 $\pm$ 3.2 |
|  | 10 | 2.2 $\pm$ 1.6 | −25.7 $\pm$ 2.6 | 136.2 $\pm$ 5.3 |
| Compound 5 | 3 | 1.3 $\pm$ 1.2 | −15.5 $\pm$ 1.6 | 57.4 $\pm$ 3.3 |
|  | 10 | 3.4 $\pm$ 1.8 | −25.9 $\pm$ 2.1 | 127.3 $\pm$ 3.7 |
| Compound 6 | 3 | 3.8 $\pm$ 1.0 | −16.1 $\pm$ 1.7 | 51.5 $\pm$ 3.1 |
|  | 10 | 7.3 $\pm$ 2.1 | −27.9 $\pm$ 1.4 | 110.9 $\pm$ 2.6 |
| Compound 7 | 3 | 2.8 $\pm$ 1.3 | −13.1 $\pm$ 1.6 | 117.6 $\pm$ 3.9 |
|  | 10 | 5.8 $\pm$ 1.7 | −26.6 $\pm$ 2.2 | 180 or longer |
| Compound 8 | 3 | 1.7 $\pm$ 1.6 | −14.6 $\pm$ 2.6 | 67.1 $\pm$ 3.8 |
|  | 10 | 3.5 $\pm$ 1.4 | −26.1 $\pm$ 2.3 | 161.0 $\pm$ 2.1 |
| Compound 9 | 3 | −3.0 $\pm$ 2.5 | −17.5 $\pm$ 2.2 | 86.6 $\pm$ 6.7 |
|  | 10 | −7.2 $\pm$ 3.8 | −27.2 $\pm$ 3.1 | 180 or longer |
| Compound 10 | 3 | −3.7 $\pm$ 1.3 | −18.1 $\pm$ 2.9 | 73.2 $\pm$ 4.2 |
|  | 10 | −6.5 $\pm$ 2.5 | −30.6 $\pm$ 3.2 | 180 or longer |
| Compound 11 | 3 | 2.4 $\pm$ 1.3 | −15.0 $\pm$ 2.0 | 48.9 $\pm$ 3.1 |
|  | 10 | 3.6 $\pm$ 1.4 | −29.2 $\pm$ 2.1 | 91.2 $\pm$ 5.8 |
| Compound 12 | 3 | 2.7 $\pm$ 1.8 | −19.1 $\pm$ 2.0 | 82.0 $\pm$ 3.1 |
|  | 10 | 7.9 $\pm$ 2.8 | −31.4 $\pm$ 3.3 | 180 or longer |
| Compound 13 | 3 | −3.5 $\pm$ 2.4 | −17.1 $\pm$ 2.8 | 82.5 $\pm$ 3.9 |
|  | 10 | −8.2 $\pm$ 1.6 | −28.8 $\pm$ 2.4 | 163.2 $\pm$ 4.3 |
| Compound 14 | 3 | 1.7 $\pm$ 1.1 | −15.6 $\pm$ 2.8 | 73.5 $\pm$ 5.3 |
|  | 10 | 3.9 $\pm$ 1.0 | −29.0 $\pm$ 3.0 | 180 or longer |
| Compound 15 | 3 | 5.8 $\pm$ 3.7 | −24.3 $\pm$ 1.4 | 149.1 $\pm$ 1.4 |
|  | 10 | 8.2 $\pm$ 1.7 | −39.4 $\pm$ 2.0 | 180 or longer |

TABLE 1-continued

| Compound | Dosage μg/kg i.v. | Heart Rate ΔHeart Rate/ min. ± S.E. | Hypotensive Effect Mean Blood Pressure ΔmmHg ± S.E. | Duration min. ± S.E. |
|---|---|---|---|---|
| Compound 16 | 3 | −6.0 ± 3.2 | −19.6 ± 3.7 | 98.3 ± 6.2 |
|  | 10 | −11.0 ± 2.9 | −31.8 ± 3.4 | 180 or longer |
| Compound 17 | 3 | 4.8 ± 2.1 | −13.0 ± 3.6 | 44.1 ± 3.6 |
|  | 10 | 7.5 ± 3.6 | −23.3 ± 2.9 | 108.6 ± 4.5 |
| Compound 18 | 3 | 2.8 ± 1.7 | −20.2 ± 3.7 | 139.1 ± 4.3 |
|  | 10 | 6.1 ± 3.5 | −36.4 ± 3.1 | 180 or longer |
| Compound 19 | 3 | 1.7 ± 1.3 | −14.7 ± 1.7 | 64.4 ± 3.7 |
|  | 10 | 4.9 ± 1.4 | −26.5 ± 2.3 | 152.1 ± 4.3 |

As is clear from Table 1, it is observed with each compound that the increase and decrease of the heart rate is slight and a good hypotensive effect is retained for such long period of time as 1.5–3 hours, or 3 hours or longer, at an amount equivalent to the dosage, for example 10 μg/kg. With the compounds of the present invention [I] other than those described in Table 1, e.g., the compounds described in Examples hereinbelow described, a hypotensive effect having a duration of about 1.5 hours or longer was also observed. Further, in the test on the vasodilating effect separately carried out using anesthetized dogs, the compounds of the present invention [I] showed a long-lasting significant activity.

The compounds of the present invention [I] may be produced by reacting a dihydropyridine derivative of the general formula:

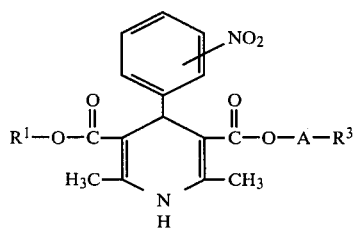

[II]

wherein $R^1$ and A are as defined above, and $R^3$ represents a halogen, a mesyloxy group, a tosyloxy group or a benzenesulfonyloxy group, with a 5-pyrazolone derivative of the general formula:

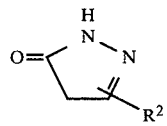

[III]

wherein $R^2$ is as defined above, using an anionizing reagent and, depending on the necessity, an alkali metal iodide (hereinafter this is referred to as Process 1). The reaction of this Process 1 advantageously proceeds by adding the dihydropyridine derivative [II] to a reaction mixture of the 5-pyrazolone derivative [III] and the anionizing reagent.

As the anionizing reagent, there may be included alkaline metals such as metallic sodium, metallic potassium etc., alkaline earth metals such as metallic calcium, metallic magnesium etc., alkali metal hydrides such as sodium hydride, potassium hydride, lithium hydride etc., carbonates such as sodium carbonate, potassium carbonate etc., sodium or potassium alkoxides such as with methanol, ethanol, propanol, butanol etc., and tertiary amines such as triethylamine, pyridine, dimethylaniline etc. In the above-described reaction, where an alkoxide is employed as the anionizing reagent, it is advantageous to remove as much alcohol produced as possible. As the alkali metal iodide, there may be included sodium iodide or potassium iodide. The alkali metal iodide promotes the above-described reaction where a dihydropyridine derivative in which $R^3$ in the general formula [II] is a halogen other than iodine is employed as the starting material.

The reaction ratio is such that the 5-pyrazolone derivative [III] is employed in an amount of 1–6 moles, preferably 1–2 moles, per mole of the dihydropyridine derivative [II]. Similarly, the ratio of the anionizing reagent, where the above-described reagent other than the tertiary amine is employed, is the equimolar amount to or more than that of the dihydropyridine derivative [II] employed but not more than the equimolar amount to that of the 5-pyrazolone derivative [III] employed, while where the tertiary amine is employed, this is not less than the equimolar amount to that of the dihydropyridine derivative [II] employed.

As the reaction solvent, there may be employed dimethylsulfoxide, N,N-dimethylformamide, N,N-dimethylacetamide, pyridine, dioxane, hexamethylphosphoric triamide, N-methylmorpholine, 1,2-dimethoxyethane, or a mixture of two or more thereof. While the reaction temperature may be established in the rage of 0°–180° C., the range of 15°–100° C. is suitable.

The compounds of the present invention [I] produced by the above-described reaction may be purified by such purifying method as column chromatography using an ion exchange resin, silica gel etc. as a carrier, crystallization, fractional precipitation, recrystallization, or an appropriate combination of these.

Furthermore, in Process 1, a compound of the general formula:

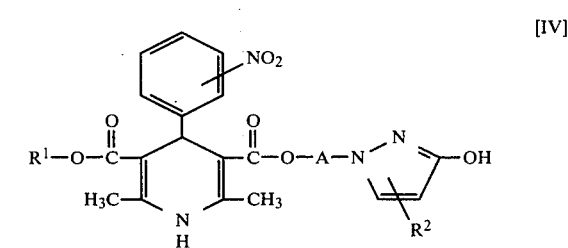

[IV]

wherein $R^1$, $R^2$ and A are as defined above, may be obtained as a by-product. This compound [IV] also showed useful pharmacological activity, such as long-lasting hypotensive effect and vasodilating effect.

Alternatively, the compounds of the present invention [I] may also be produced by processes other than Process 1, which are illustrated by the following reaction schemes.

[Process 2]

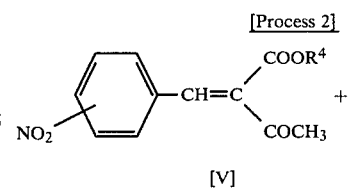

[V]

-continued

[Process 2]

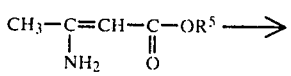

[VI]

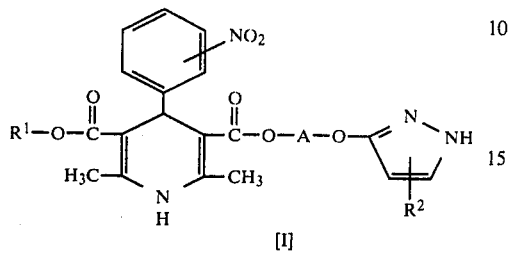

[I]

wherein $R^1$, $R^2$ and A are as defined above, and $R^4$ and $R^5$ each represents $R^1$ or a group represented by the general formula:

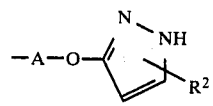

(wherein $R^2$ and A are as defined above), with the proviso that $R^4$ and $R^5$ are not the same.

[Process 3]

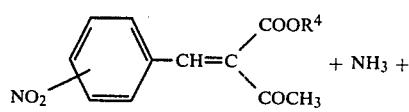

[V]

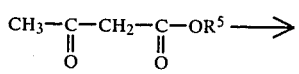

[VII]

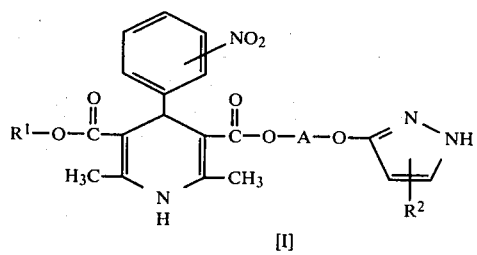

[I]

wherein $R^1$, $R^2$, $R^4$, $R^5$ and A are as defined above.

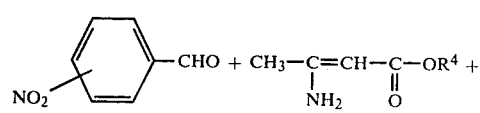

[IX]          [VIII]

-continued

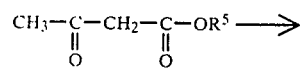

[VII]

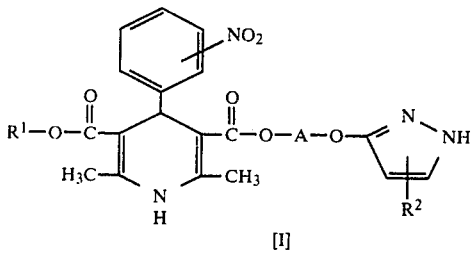

[I]

wherein $R^1$, $R^2$, $R^4$, $R^5$ and A are as defined above.

As the reaction solvent in Processes 2–4, there may be employed alcohols such as methanol, ethanol, isopropanol, butanol, etc., diols such as ethylene glycol, propylene glycol etc., cellosolves such as methyl cellosolve, propyl cellosolve, ethyl cellosolve etc., nitriles such as acetonitrile, propionitrile etc., nitrobenzene, N,N-dimethylacetamide, N,N-dimethylformamide, pyridine, hexamethylphosphoric triamide or a mixed solvent consisting of two or more of these. Further, as a reaction accelerator, molecular sieves, piperidine, diethylamine, triethylamine, N,N-dimethylaniline or the like may appropriately be used. The reaction temperature may be established in the range of 50°–180° C.

The compounds of the present invention [I] produced by these processes may also be purified using the purifying method described in Process 1.

In Process 1, the dihydropyridine derivative represented by the above general formula [II] which is used as one starting material, when it is a compound in which $R^3$ is a halogen, that is, a compound of the general formula:

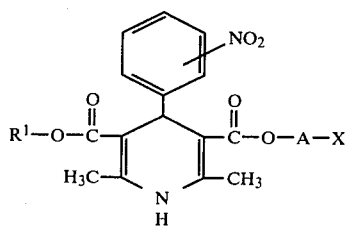

[X]

wherein $R^1$ and A are as defined above, and X represents a halogen, may be produced by one of the following three processes:

reacting a compound of the general formula:

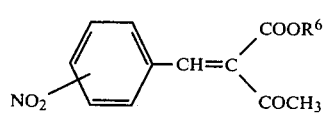

[XI]

wherein $R^6$ represents $R^1$ or a group represented by the general formula: —A—X (wherein A and X are as defined above), with a compound of the general formula:

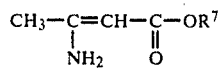

wherein $R^7$ represents $R^1$ or a group represented by the general formula: —A—X (wherein A and X are as defined above), with the proviso that $R^7$ and $R^6$ are not the same;

reacting a compound of the general formula [XI] with ammonia and a compound of the general formula:

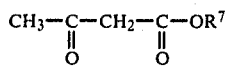

wherein $R^7$ is as defined above; or reacting the aforementioned nitrobenzaldehyde of the general formula:

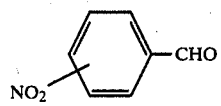

with the compound of the general formula [XIII] and a compound of the general formula:

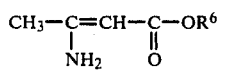

wherein $R^6$ is as defined above.

In the respective reactions described above, the reaction solvent, the reaction accelerator and the reaction temperature may be employed or established from those described in the above Processes 2–4.

The dihydropyridine derivative [II] other than that of the general formula [X], that is, the compound of the general formula:

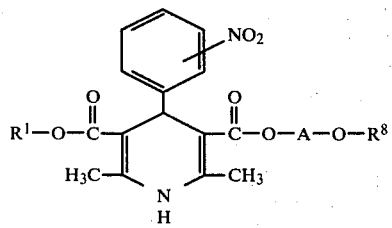

wherein $R^1$ and A are as defined above, and $R^8$ represents a mesyl group, a tosyl group or a benzenesulfonyl group, may be produced by reacting a compound of the general formula:

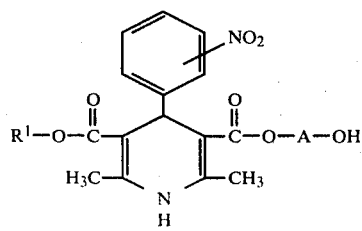

wherein $R^1$ and A are as defined above, with mesyl chloride, tosyl chloride or benzenesulfonyl chloride.

As the reaction solvent, there may be employed chloroform, dichloromethane, ethyl acetate, methyl acetate, N,N-dimethylformamide, dimethylsulfoxide etc. as well as a mixed solvent of two or more of these, and as the acid scavenger, there may be employed pyridine, lutidine, triethylamine, N,N-dimethylaniline and the like bases. The reaction temperature is preferably established in the range of $-10°$ to $30°$ C.

The commpound of the general formula [XV] may be produced similarly as in the above-described processes for producing the compound of the general formula [X], except that compounds where the halogen represented by X in the above general formulae [XI], [XII], [XIII] and [XIV] is replaced by a hydroxyl group.

In Process 1, the 5-pyrazolone derivative of the above general formula [III] which is employed as the other starting material may be produced by a process according to the known processes for producing 5-pyrazolone derivatives, for example, the process described in Berichte Der Deutschen Chemischen Gesellschaft, Vol. 29, p. 253.

In the starting materials employed in Processes 2–4, the compound of the above general formula [VII] may be produced using a compound of the general formula: $R^5$—OH (wherein $R^5$ is as defined above) and diketene by a process according to the known processes for producing acetoacetate derivatives, for example, the process described in the Journal of the Chemical Society, Vol. 97, p. 1978, 1910. Similarly, both compounds of the above general formulae [VI] and [VIII] may be produced using a compound of the general formula:

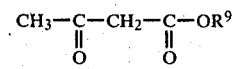

wherein $R^9$ represents $R^4$ or $R^5$ defined above, and ammonia by a process according to the known processes for producing enaminocarboxylate derivatives, for example, the process described in the Journal of the American Chemical Society, Vol. 67, p. 1017, 1945. Further, the compound of the above general formula [V] may be produced using the compound of the above general formula [IX] and a compound of the general formula:

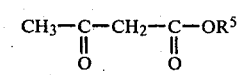

wherein $R^5$ is as defined above, by a process according to the known processes for producing benzylideneacetoacetate derivatives, for example, the process described in Organic Syntheses Collective Volume, Vol. 4, p. 408, 1963.

PREPARATION 1

(Step i)

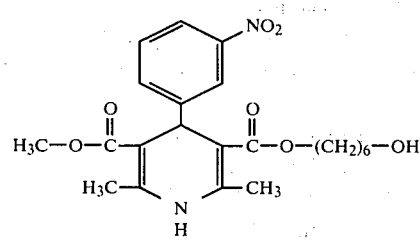

141.8 g (1.20 mole) of 1,6-hexanediol and 1.0 g (0.01 mole) of triethylamine were dissolved in 60 ml of ethyl acetate with heating, 25.2 g (0.30 mole) of diketene was added dropwise thereto, and heating at reflux was conducted for an hour. The reaction mixture was cooled to 15° C., then 400 ml of benzene was added thereto, and the excess 1,6-hexanediol which had separated out as white crystals was filtered off. The obtained filtrate was concentrated under reduced pressure to obtain 49.2 g of 6-hydroxyhexyl acetoacetate as an oil. 40.5 g (0.20 mole) of this compound was dissolved along with 30.2 g (0.20 mole) of m-nitrobenzaldehyde and 23.0 g (0.20 mole) of methyl β-aminocrotonate in 300 ml of ethanol, and heating at reflux was conducted for 5 hours. After cooling, the ethanol was distilled off under reduced pressure, the resulting residue was dissolved in 300 ml of ethyl acetate, washed with 1000 ml of water twice, and dried over anhydrous sodium sulfate. This solution, after concentration under reduced pressure, was subjected to column chromatography using silica gel, and the impurities-free fractions in the fixed phase were eluted using a mixed solution of benzene-ethyl acetate (the ratio by volume of 1:1). The obtained eluate was concentrated to dryness under reduced pressure to obtain 51.8 g (0.12 mole; yield 60.0%) of a pale yellow crystalline powder of the 1,4-dihydro-2,6-dimethyl-4-(3-nitrophenyl)pyridine-3,5-dicarboxylic acid 3-methyl ester 5-(6-hydroxyhexyl) ester represented by the above structural formula.

PMR Spectrum $(CDCl_3+D_2O)\delta$: 1.00–2.00 (8H, m), 2.30 (6H, s), 3.58 (3H, s), 3.30–3.75 (2H), 5.00 (1H, s), 7.07–8.07 (4H, m).

By procedures similar to the above, the following compounds were produced in yields of 15.4–82.0%.

1,4-Dihydro-2,6-dimethyl-4-(3-nitrophenyl)pyridine-3,5-dicarboxylic acid 3-normalpropyl ester 5-(6-hydroxyhexyl) ester;

1,4-Dihydro-2,6-dimethyl-4-(3-nitrophenyl)pyridine-3,5-dicarboxylic acid 3-isobutyl ester 5-(6-hydroxyhexyl) ester;

1,4-Dihydro-2,6-dimethyl-4-(3-nitrophenyl)pyridine-3,5-dicarboxylic acid 3-(2-methoxyethyl) ester 5-(6-hydroxyhexyl) ester;

1,4-Dihydro-2,6-dimethyl-4-(3-nitrophenyl)pyridine-3,5-dicarboxylic acid 3-(2-isopropoxyethyl) ester 5-(6-hydroxyhexyl) ester;

1,4-Dihydro-2,6-dimethyl-4-(3-nitrophenyl)pyridine-3,5-dicarboxylic acid 3-(2-normalpropoxyethyl) ester 5-(6-hydroxyhexyl) ester;

1,4-Dihydro-2,6-dimethyl-4-(3-nitrophenyl)pyridine-3,5-dicarboxylic acid 3-(2-isobutoxyethyl) ester 5-(6-hydroxylhexyl) ester;

1,4-Dihydro-2,6-dimethyl-4-(2-nitrophenyl)pyridine-3,5-dicarboxylic acid 3-methyl ester 5-(6-hydroxyhexyl) ester;

1,4-Dihydro-2,6-dimethyl-4-(2-nitrophenyl)pyridine-3,5-dicarboxylic acid 3-ethyl ester 5-(6-hydroxyhexyl) ester;

1,4-Dihydro-2,6-dimethyl-4-(2-nitrophenyl)pyridine-3,5-dicarboxylic acid 3-isopropyl ester 5-(6-hydroxyhexyl) ester;

1,4-Dihydro-2,6-dimethyl-4-(2-nitrophenyl)pyridine-3,5-dicarboxylic acid 3-(2-methoxyethyl) ester 5-(6-hydroxyhexyl) ester;

1,4-Dihydro-2,6-dimethyl-4-(2-nitrophenyl)pyridine-3,5-dicarboxylic acid 3-(2-isopropoxyethyl) ester 5-(6-hydroxyhexyl) ester;

1,4-Dihydro-2,6-dimethyl-4-(3-nitrophenyl)pyridine-3,5-dicarboxylic acid 3-methyl ester 5-(6-hydroxy-1,6-diisopropylhexyl) ester;

1,4-Dihydro-2,6-dimethyl-4-(3-nitrophenyl)pyridine-3,5-dicarboxylic acid 3-methyl ester 5-(6-hydroxy-5,5-dimethylhexyl) ester;

1,4-Dihydro-2,6-dimethyl-4-(2-nitrophenyl)pyridine-3,5-dicarboxylic acid 3-methyl ester 5-(6-hydroxy-1,6-dimethylhexyl) ester;

1,4-Dihydro-2,6-dimethyl-4-(2-nitrophenyl)pyridine-3,5-dicarboxylic acid 3-methyl ester 5-(6-hydroxy-1,6-diethylhexyl) ester;

1,4-Dihydro-2,6-dimethyl-4-(3-nitrophenyl)pyridine-3,5-dicarboxylic acid 3-ethyl ester 5-(6-hydroxy-1,6-dimethylhexyl) ester;

1,4-Dihydro-2,6-dimethyl-4-(3-nitrophenyl)pyridine-3,5-dicarboxylic acid 3-ethyl ester 5-(6-hydroxy-3,4-dimethylhexyl) ester;

1,4-Dihydro-2,6-dimethyl-4-(2-nitrophenyl)pyridine-3,5-dicarboxylic acid 3-ethyl ester 5-(6-hydroxy-5-methylhexyl) ester;

1,4-Dihydro-2,6-dimethyl-4-(2-nitrophenyl)pyridine-3,5-dicarboxylic acid 3-ethyl ester 5-(6-hydroxy-2,5-diisopropylhexyl) ester;

1,4-Dihydro-2,6-dimethyl-4-(2-nitrophenyl)pyridine-3,5-dicarboxylic acid 3-(2-methoxyethyl) ester 5-(6-hydroxy-2,5-dimethylhexyl) ester;

1,4-Dihydro-2,6-dimethyl-4-(3-nitrophenyl)pyridine-3,5-dicarboxylic acid 3-methyl ester 5-(6-hydroxy-1-methylhexyl) ester;

1,4-Dihydro-2,6-dimethyl-4-(3-nitrophenyl)pyridine-3,5-dicarboxylic acid 3-ethyl ester 5-(6-hydroxyhexyl) ester;

1,4-Dihydro-2,6-dimethyl-4-(3-nitrophenyl)pyridine-3,5-dicarboxylic acid 3-isopropyl ester 5-(6-hydroxyhexyl) ester.

These compounds described above were obtained as a pale yellow crystalline powder or a pale yellow oil. The PMR spectrum and the IR spectrum of each powder or oil thus obtained supported the structural formula expressed by the above chemical name.

(Step ii)

43.3 g (0.10 mole) of the 1,4-dihydro-2,6-dimethyl-4-(3-nitrophenyl)pyridine-3,5-dicarboxylic acid 3-methyl ester 5-(6-hydroxyhexyl) ester produced in Step i described above was dissolved along with 29.5 g (0.16 mole) of tosyl chloride in 200 ml of chloroform, to which was added dropwise 25.0 g (0.32 mole) of pyridine with stirring under ice cooling. This reaction mixture was allowed to stand at room temperature for 2 hours, then, after adding 100 ml of water, was stirred for 3 hours. The chloroform layer of the obtained liquid was separated, washed with 200 ml of 0.02 N sulfuric acid, 200 ml of water and 200 ml of saturated aqueous sodium bicarbonate successively, and dried over anhydrous sodium sulfate. This chloroform solution was chromatographed on a silica gel column using a mixed solution of benzene-ethyl acetate (the ratio by volume of 8:1) as an eluent to obtain 36.6 g (yield 62.5%) of the 1,4-dihydro-2,6-dimethyl-4-(3-nitrophenyl)pyridine-3,5-dicarboxylic acid 3-methyl ester 5-(6-tosyloxyhexyl) ester as a pale yellow oil.

PMR Spectrum (CDCl$_3$)δ: 1.00–2.00 (8H, m), 2.30 (6H, s), 2.38 (3H, s), 3.57 (3H, s), 3.73–4.13 (4H), 5.00 (1H, s), 6.19 (1H, s), 7.09–8.07 (8H, m).

By procedures similar to the above, the following compounds were produced in yields of 30.6–73.8%.

1,4-Dihydro-2,6-dimethyl-4-(3-nitrophenyl)pyridine-3,5-dicarboxylic acid 3-normalpropyl ester 5-(6-tosyloxyhexyl) ester;
1,4-Dihydro-2,6-dimethyl-4-(3-nitrophenyl)pyridine-3,5-dicarboxylic acid 3-isobutyl ester 5-(6-tosyloxyhexyl) ester;
1,4-Dihydro-2,6-dimethyl-4-(3-nitrophenyl)pyridine-3,5-dicarboxylic acid 3-(2-methoxyethyl) ester 5-(6-tosyloxyhexyl) ester;
1,4-Dihydro-2,6-dimethyl-4-(3-nitrophenyl)pyridine-3,5-dicarboxylic acid 3-(2-isopropoxyethyl) ester 5-(6-tosyloxyhexyl) ester;
1,4-Dihydro-2,6-dimethyl-4-(3-nitrophenyl)pyridine-3,5-dicarboxylic acid 3-(2-normalpropoxyethyl) ester 5-(6-tosyloxyhexyl) ester;
1,4-Dihydro-2,6-dimethyl-4-(3-nitrophenyl)pyridine-3,5-dicarboxylic acid 3-(2-isobutoxyethyl) ester 5-(6-tosyloxyhexyl) ester;
1,4-Dihydro-2,6-dimethyl-4-(2-nitrophenyl)pyridine-3,5-dicarboxylic acid 3-methyl ester 5-(6-tosyloxyhexyl) ester;
1,4-Dihydro-2,6-dimethyl-4-(2-nitrophenyl)pyridine-3,5-dicarboxylic acid 3-ethyl ester 5-(6-toxyloxyhexyl) ester;
1,4-Dihydro-2,6-dimethyl-4-(2-nitrophenyl)pyridine-3,5-dicarboxylic acid 3-isopropyl ester 5-(6-tosyloxyhexyl) ester;
1,4-Dihydro-2,6-dimethyl-4-(2-nitrophenyl)pyridine-3,5-dicarboxylic acid 3-(2-methoxyethyl) ester 5-(6-tosyloxyhexyl) ester;
1,4-Dihydro-2,6-dimethyl-4-(2-nitrophenyl)pyridine-3,5-dicarboxylic acid 3-(2-isopropoxyethyl) ester 5-(6-tosyloxyhexyl) ester;
1,4-Dihydro-2,6-dimethyl-4-(3-nitrophenyl)pyridine-3,5-dicarboxylic acid 3-methyl ester 5-(6-tosyloxy-1,6-diisopropylhexyl) ester;
1,4-Dihydro-2,6-dimethyl-4-(3-nitrophenyl)pyridine-3,5-dicarboxylic acid 3-methyl ester 5-(6-tosyloxy-5,5-dimethylhexyl) ester;
1,4-Dihydro-2,6-dimethyl-4-(2-nitrophenyl)pyridine-3,5-dicarboxylic acid 3-methyl ester 5-(6-tosyloxy-1,6-dimethylhexyl) ester;
1,4-Dihydro-2,6-dimethyl-4-(2-nitrophenyl)pyridine-3,5-dicarboxylic acid 3-methyl ester 5-(6-tosyloxy-1,6-diethylhexyl) ester;
1,4-Dihydro-2,6-dimethyl-4-(3-nitrophenyl)pyridine-3,5-dicarboxylic acid 3-ethyl ester 5-(6-tosyloxy-1,6-dimethylhexyl) ester;
1,4-Dihydro-2,6-dimethyl-4-(3-nitrophenyl)pyridine-3,5-dicarboxylic acid 3-ethyl ester 5-(6-tosyloxy-3,4-dimethylhexyl) ester;
1,4-Dihydro-2,6-dimethyl-4-(2-nitrophenyl)pyridine-3,5-dicarboxylic acid 3-ethyl ester 5-(6-tosyloxy-5-methylhexyl) ester;
1,4-Dihydro-2,6-dimethyl-4-(2-nitrophenyl)pyridine-3,5-dicarboxylic acid 3-ethyl ester 5-(6-tosyloxy-2,5-diisopropylhexyl) ester;
1,4-Dihydro-2,6-dimethyl-4-(2-nitrophenyl)pyridine-3,5-dicarboxylic acid 3-(2-methoxyethyl) ester 5-(6-tosyloxy-2,5-dimethylhexyl) ester;
1,4-Dihydro-2,6-dimethyl-4-(3-nitrophenyl)pyridine-3,5-dicarboxylic acid 3-methyl ester 5-(6-tosyloxy-1-methylhexyl) ester;
1,4-Dihydro-2,6-dimethyl-4-(3-nitrophenyl)pyridine-3,5-dicarboxylic acid 3-ethyl ester 5-(6-tosyloxyhexyl) ester;
1,4-Dihydro-2,6-dimethyl-4-(3-nitrophenyl)pyridine-3,5-dicarboxylic acid 3-isopropyl ester 5-(6-tosyloxyhexyl) ester.

These compounds described above were obtained as a pale yellow oil. The PMR spectrum and the IR spectrum of each oil thus obtained supported the structural formula expressed by the above chemical name.

PREPARATION 2

Similar procedures were repeated except that, in Step ii of Preparation 1, the tosyl chloride was replaced by mesyl chloride or benzenesulfonyl chloride, to obtain 1,4-dihydro-2,6-dimethyl-4-(3-nitrophenyl)pyridine-3,5-dicarboxylic acid 3-methyl ester 5-(6-mesyloxyhexyl) ester or 1,4-dihydro-2,6-dimethyl-4-(3-nitrophenyl)-pyridine-3,5-dicarboxylic acid 3-methyl ester 5-(6-benzenesulfonyloxyhexyl) ester.

PREPARATION 3

22.1 g (0.10 mole) of 6-chlorohexyl acetoacetate, 15.1 g (0.10 mole) of m-nitrobenzaldehyde and 11.5 g (0.10 mole) of methyl β-aminocrotonate were dissolved in 50 ml of ethanol, and heating at reflux was conducted for 5 hours. After cooling, the reaction solvent was evaporated under reduced pressure, and the resulting oily residue was purified by silica gel column chromatography using a mixed solution of chloroform-methanol (the ratio by volume of 140:1) as an eluent to obtain 29.0 g (yield 64.3%) of a pale yellow crystalline powder of the 1,4-dihydro-2,6-dimethyl-4-(3-nitrophenyl)pyridine-3,5-dicarboxylic acid 3-methyl ester 5-(6-chlorohexyl) ester.

PMR Spectrum (CDCl$_3$)δ: 1.03–1.93 (8H, m), 2.30 (6H, s), 3.40 (2H, t), 3.57 (3H, s), 3.96 (2H, t), 5.00 (1H, s), 6.14 (1H, s), 7.03–8.07 (4H, m).

By procedures similar to the above, the following compounds were produced as a pale yellow crystalline powder in yields of 45.3–70.5%.

1,4-Dihydro-2,6-dimethyl-4-(3-nitrophenyl)pyridine-3,5-dicarboxylic acid 3-methyl ester 5-(6-chloro-1-methylhexyl) ester;
1,4-Dihydro-2,6-dimethyl-4-(2-nitrophenyl)pyridine-3,5-dicarboxylic acid 3-ethyl ester 5-(6-chloro-5-methylhexyl) ester;
1,4-Dihydro-2,6-dimethyl-4-(3-nitrophenyl)pyridine-3,5-dicarboxylic acid 3-normalpropyl ester 5-(6-chlorohexyl) ester;
1,4-Dihydro-2,6-dimethyl-4-(3-nitrophenyl)pyridine-3,5-dicarboxylic acid 3-isopropyl ester 5-(6-chlorohexyl) ester;

1,4-Dihydro-2,6-dimethyl-4-(3-nitrophenyl)pyridine-3,5-dicarboxylic acid 3-(2-methoxyethyl) ester 5-(6-chlorohexyl) ester;

1,4-Dihydro-2,6-dimethyl-4-(3-nitrophenyl)pyridine-3,5-dicarboxylic acid 3-(2-isopropoxyethyl) ester 5-(6-chlorohexyl) ester.

The respective final products described in Step i and Step ii in Preparation 1, Preparation 2 and Preparation 3 were not only useful as the intermediates for the synthesis of the compounds of the present invention [I] but also exhibited pharmacological activity which makes them useful as they are, such as hypotensive effect, vasodilating effect or platelet aggregation inhibiting effect.

EXAMPLE 1

(Compound 1)

0.24 g (10 mmole) of sodium hydride was suspended in 10 ml of dimethylsulfoxide, to which was added gradually 1.00 g (10 mmole) of 3-methyl-5-pyrazolone with stirring at room temperature. After evolution of hydrogen had ceased, to this solution was added dropwise 30 ml of a solution of 5.87 g (10 mmole) of 1,4-dihydro-2,6-dimethyl-4-(3-nitrophenyl)pyridine-3,5-dicarboxylic acid 3-methyl ester 5-(6-tosyloxyhexyl) ester in dimethylsulfoxide, and the mixture was stirred at room temperature for 2 hours. The resulting reaction mixture was poured into 2000 ml of ice water, and the separated product was extracted with 100 ml of chloroform. This chloroform solution was washed with 50 ml of water 5 times, dried over anhydrous sodium sulfate, and then concentrated under reduced pressure to obtain a brown oily residual liquid. This residual liquid was purified by silica gel column chromatography using a mixed solution of benzene-ethyl acetate (the ratio by volume of 1:1) as an eluent to obtain 3.20 g (yield 62.4%) of a pale yellow powder of the 1,4-dihydro-2,6-dimethyl-4-(3-nitrophenyl)pyridine-3,5-dicarboxylic acid 3-methyl ester 5-[6-(5-methyl-3-pyrazolyloxy)hexyl]ester.

IR Spectrum (CHCl$_3$) cm$^{-1}$: 3490, 3460, 2940, 1690, 1520, 1340, 1220, 1118.

PMR Spectrum (CDCl$_3$+D$_2$O)δ: 1.10–1.19(8H,m), 2.20(3H,s), 2.33(6H,s), 3,60(3H,s), 4.00(4H,t), 5.02(1H,s), 5.37(1H,s), 7.00–8.10(4H,m).

Analysis for C$_{26}$H$_{32}$N$_4$O$_7$: Calcd. (%): C,60.93; H,6.29; N,10.93. Found (%): C,61.13; H,6.43; N,10.75.

Procedures similar to the above were repeated, except that the 3-methyl-5-pyrazolone and the 1,4-dihydro-2,6-dimethyl-4-(3-nitrophenyl)pyridine-3,5-dicarboxylic acid 3-methyl ester 5-(6-tosyloxyhexyl) ester were replaced by the corresponding compounds and further the sodium hydride was replaced, depending on the necessity, by other appropriate anionizing reagents, to obtain the compounds in Examples 2–13 below.

EXAMPLE 2

1,4-Dihydro-2,6-dimethyl-4-(3-nitrophenyl)pyridine-3,5-dicarboxylic acid 3-methyl ester 5-[6-(5-methyl-3-pyrazolyloxy)-1,6-diisopropylhexyl]ester Aspect: Pale yellow powder.

IR Spectrum (CHCl$_3$) cm$^{-1}$: 3490, 3460, 2940, 1690, 1520, 1340.

PRM Spectrum (CDCl$_3$)δ: 3.60(3H,s), 5.10(1H,s), 5.40(1H,s).

Analysis for C$_{32}$H$_{44}$N$_4$O$_7$: Calcd. (%): C,64.41; H,7.43; N,9.39. Found (%): C,64.81; H,7.76; N,9.05.

EXAMPLE 3

(Compound 2)

1,4-Dihydro-2,6-dimethyl-4-(3-nitrophenyl)pyridine-3,5-dicarboxylic acid 3-methyl ester 5-[6-(5-isopropyl-3-pyrazolyloxy)hexyl]ester Aspect: Pale yellow powder.

IR Spectrum (CHCl$_3$) cm$^{-1}$: 3490, 3460, 2940, 1690, 1520, 1340, 1220.

PMR Spectrum (CDCl$_3$+D$_2$O)δ: [1.00–1.90(8H,m) and 1.20(6H,d); total 14H], 2.30(6H,s), 2.55–3.00(1H,m), 3.57(3H,s), 4.00(4H,t), 5.01(1H,s), 5.38(1H,s), 7.05–8.07(4H,m).

Analysis for C$_{28}$H$_{36}$N$_4$O$_7$: Calcd. (%): C,62.21; H,6.71; N,10.36. Found (%): C,62.35; H,6.82; N,10.35.

EXAMPLE 4

(Compound 3)

1,4-Dihydro-2,6-dimethyl-4-(3-nitrophenyl)pyridine-3,5-dicarboxyic acid 3-ethyl ester 5-[6-(5-methyl-3-pyrazolyloxy)hexyl]ester Aspect: Pale yellow powder.

IR Spectrum (CHCl$_3$) cm$^{-1}$: 3490, 3470, 2980, 2940, 1695, 1520.

PMR Spectrum (CDCl$_3$+D$_2$O)δ: 1.07–1.87(8H,m), 1.22(3H,t), 2.18(3H,s), 2.30(6H,s), 3.80–4.23(6H,m), 5.00(1H,s), 5.35(1H,s), 7.15–8.07(4H,m).

Analysis for C$_{27}$H$_{34}$N$_4$O$_7$: Calcd. (%): C,61.58; H,6.51; N,10.64. Found (%): C,61.71; H,6.49; N,10.49.

EXAMPLE 5

1,4-Dihydro-2,6-dimethyl-4-(3-nitrophenyl)pyridine-3,5-dicarboxylic acid 3-ethyl ester 5-[6-(5-isopropyl-3-pyrazolyloxy)-3,4-dimethylhexyl]ester Aspect: Pale yellow powder.

IR Spectrum (CHCl$_3$) cm$^{-1}$: 3490, 3460, 2940, 1690, 1520, 1340.

PMR Spectrum (CDCl$_3$+D$_2$O)δ: 0.65–1.95(21H,m), 2.30(6H,s), 2.55–3.00(1H,m), 3.80–4.21(6H,m), 5.09(1H,s), 5.38(1H,s), 7.02–8.07(4H,m).

Analysis for C$_{31}$H$_{42}$N$_4$O$_7$: Calcd. (%): C,63.90; H,7.27; N,9.62. Found (%): C,64.27; H,7.58; N,9.90.

EXAMPLE 6

1,4-Dihydro-2,6-dimethyl-4-(3-nitrophenyl)pyridine-3,5-dicarboxylic acid 3-ethyl ester 5-[6-(5-hexyl-3-pyrazolyloxy)hexyl]ester Aspect: Pale yellow powder.

IR Spectrum (CHCl$_3$) cm$^{-1}$: 3490, 3460, 1685, 1340.

PMR Spectrum (CDCl$_3$+D$_2$O)δ: 0.55–2.00(22H,m), [2.30(6H,s) and 2.30–2.70(2H); total 8H], 3.80–4.23(6H,m), 5.10(1H,s), 5.37(1H,s), 7.02–8.05(4H,m).

Analysis for C$_{32}$H$_{44}$N$_4$O$_7$: Calcd. (%): C,64.41; H,7.43; N,9.39. Found (%): C,64.89; H,7.22; N,9.68.

EXAMPLE 7

(Compound 4)

1,4-Dihydro-2,6-dimethyl-4-(3-nitrophenyl)pyridine-3,5-dicarboxylic acid 3-isopropyl ester 5-[6-(5-methyl-3-pyrazolyloxy)hexyl]ester Aspect: Pale yellow powder.

IR Spectrum (CHCl$_3$) cm$^{-1}$: 3490, 3460, 2940, 1690, 1520, 1340, 1220.

PMR Spectrum (CDCl$_3$+D$_2$O) δ: [1.10(3H,d), 1.25(3H,d) and 1.00-1.95(8H,m); total 14H], 2.20(3H,s), 2.30(6H,s), 3.97(4H,t), [4.60-5.05(1H,m) and 5.00(1H,s); total 2H], 5.00(1H,s), 5.37(1H,s), 7.05-8.07(4H,m).

Analysis for C$_{28}$H$_{36}$N$_4$O$_7$: Calcd. (%): C,62.21; H,6.71; N,10.36. Found (%): C,62.40; H,6.92; N,10.44.

EXAMPLE 8

1,4-Dihydro-2,6-dimethyl-4-(3-nitrophenyl)pyridine-3,5-dicarboxylic acid 3-isopropyl ester 5-[6-(5-octyl-3-pyrazolyloxy)hexyl]ester Aspect: Pale yellow powder.

IR Spectrum (CHCl$_3$) cm$^{-1}$: 3490, 3460, 1690, 1520, 1340.

PMR Spectrum (CDCl$_3$)δ: 0.55-2.03(29H,m), 2.30(6H,s), 2.30-2.70(2H), 3.70-4.23(4H,m), 4.60-5.05(1H,m), 5.10(1H,s).

Analysis for C$_{35}$H$_{50}$N$_4$O$_7$: Calcd. (%): C,65.81; H,7.89; N,8.77. Found: (%): C,65.98; H,8.05; N,8.36.

EXAMPLE 9

1,4-Dihydro-2,6-dimethyl-4-(3-nitrophenyl)pyridine-3,5-dicarboxylic acid 3-isobutyl ester 5-[6-(5-isopropyl-3-pyrazolyloxy)hexyl]ester Aspect: Pale yellow powder.

IR Spectrum (CHCl$_3$) cm$^{-1}$: 3490, 3460, 2940, 1340, 1220.

PMR Spectrum (CDCl$_3$+D$_2$O)δ: [0.77(6H,dd), 1.20(6H,d) and 1.00-2.00(9H,m); total 21H], 2.30(6H,s), 2.50-3.07(1H,m), [3.67(2H,d) and 3.53-4.13(4H,m); total 6H], 5.03(1H,s), 5.33(1H,s), 7.05-8.07(4H,m).

Analysis for C$_{31}$H$_{42}$N$_4$O$_7$: Calcd. (%): C,63.90; H,7.27; N,9.62. Found (%): C,64.35; H,7.51; N,9.42.

EXAMPLE 10

(Compound 5)

1,4-Dihydro-2,6-dimethyl-4-(3-nitrophenyl)pyridine-3,5-dicarboxylic acid 3-(2-methoxyethyl) ester 5-[6-(5-methyl-3-pyrazolyloxy)hexyl]ester Aspect: Pale yellow powder.

IR Spectrum (CHCl$_3$) cm$^{-1}$: 3490, 3460, 2940, 1690, 1340.

PMR Spectrum (CDCl$_3$)δ: 1.00-2.00(8H,m), 2.30(3H,s), 2.33(6H,s), 3.32 (3H,s), 3.50(2H,t), 3.73-4.34(6H,m), 5.07(1H,s), 5.40(1H,s), 6.93(1H,s), 7.07-8.16(4H,m), 8.83(1H, broad).

Analysis for C$_{28}$H$_{36}$N$_4$O$_7$: Calcd. (%): C,60.42; H,6.52; N,10.07. Found (%): C,60.51; H,6.71; N,10.26.

EXAMPLE 11

1,4-Dihydro-2,6-dimethyl-4-(3-nitrophenyl)pyridine-3,5-dicarboxylic acid 3-(2-isopropoxyethyl) ester 5-[6-(5-octyl-3-pyrazolyloxy)hexyl]ester Aspect: Pale yellow powder.

IR Spectrum (CHCl$_3$) cm$^{-1}$: 3490, 3460, 1690, 1520, 1340.

PMR Spectrum (CDCl$_3$+D$_2$O)δ: 0.57-2.00(29H,m), 2.30(6H,s), 2.30-2.70(2H), 3.20-4.45(9H,m), 5.10(1H,s), 5.38(1H,s), 7.05-8.07(4H,m).

Analysis for C$_{37}$H$_{54}$N$_4$O$_8$: Calcd. (%): C,65.08; H,7.97; N,8.21. Found (%): C,65.49; H,8.28; N,8.02.

EXAMPLE 12

(Compound 6)

1,4-Dihydro-2,6-dimethyl-4-(2-nitrophenyl)pyridine-3,5-dicarboxylic acid 3-methyl ester 5-[6-(5-methyl-3-pyrazolyloxy)hexyl]ester Aspect: Pale yellow powder.

IR Spectrum (CHCl$_3$) cm$^{-1}$: 3490, 3455, 1685, 1515, 1345.

PMR Spectrum (CDCl$_3$+D$_2$O)δ: 1.10-2.00(8H,m), 2.04-2.40(9H), 3.55(3H,s), 3.76-4.16(4H), 5.37(1H,s), 5.67(1H,s), 6.92-7.70(4H,m).

Analysis for C$_{26}$H$_{32}$N$_4$O$_7$: Calcd. (%): C,60.93; H,6.29; N,10.93. Found (%): C,60.85; H,6.43; N,10.86.

EXAMPLE 13

1,4-Dihydro-2,6-dimethyl-4-(2-nitrophenyl)pyridine-3,5-dicarboxylic acid 3-(2-isopropoxyethyl) ester 5-[6-(5-methyl-3-pyrazolyloxy)hexyl]ester Aspect: Pale yellow powder.

IR Spectrum (CHCl$_3$) cm$^{-1}$: 3485, 3460, 1690, 1520.

PMR Spectrum (CDCl$_3$+D$_2$O)δ: [1.13(6H,d) and 0.90-1.95(8H,m); total 14H], 2.05-2.41(9H), 3.22-4.48(9H,m), 5.40(1H,s), 5.70(1H,s), 6.93-7.70(4H,m).

Analysis for C$_{30}$H$_{40}$N$_4$O$_8$: Calcd. (%): C,61.63; H,6.90; N,9.58. Found (%): C,61.96; H,7.06; N,9.89.

EXAMPLE 14

(Compound 7)

To 15 ml of a suspension of 0.36 g (15 mmole) of sodium hydride in N,N-dimethylformamide was added gradually 2.52 g (20 mmole) of 3-isopropyl-5-pyrazolone with stirring at room temperature, and the mixture was allowed to stand until evolution of hydrogen ceased. To this solution was added dropwise 15 ml of a solution of 6.01 g (10 mmole) of 1,4-dihydro-2,6-dimethyl-4-(3-nitrophenyl)pyridine-3,5-dicarboxylic acid 3-ethyl ester 5-(6-tosyloxyhexyl) ester in N,N-dimethylformamide, and the mixture was stirred at 70° C. for 2 hours. The resulting reaction mixture was poured into 200 ml of ice water, the separated product was extracted with 100 ml of ethyl acetate, and this ethyl acetate solution was washed with 50 ml of water twice, dried over anhydrous sodium sulfate, and then concentrated under reduced pressure to obtain an oily residual liquid. This liquid was subjected to column chromatography using silica gel, the impurities-free fractions in the fixed phase were eluted with a mixed solution of chloroform-methanol (the ratio by volume of 160:1), and the eluate was concentrated to dryness under reduced pressure to obtain 2.55 g (yield 46.0%) of a pale yellow powder of the 1,4-dihydro-2,6-dimethyl-4-(3-nitrophenyl)pyridine-3,5-dicarboxylic acid 3-ethyl ester 5-[6-(5-isopropyl-3-pyrazolyloxy)hexyl]ester.

IR Spectrum (CHCl$_3$) cm$^{-1}$: 3490, 3465, 2940, 1690, 1520.

PMR Spectrum (CDCl$_3$+D$_2$O)δ: [1.21(6H,d), 1.00-2.00(11H,m); total 17H], 2.30(6H,s), 2.56-3.00(1H), 3.70-4.27(6H,m), 5.00(1H,s), 5.37(1H,s), 7.00-8.07(4H,m).

Analysis for $C_{29}H_{38}N_4O_7$: Calcd. (%): C,62.80; H,6.91; N,10.10. Found (%): C,63.10; H,7.07; N, 9.82.

Procedures similar to the above were repeated, except that the 3-isopropyl-5-pyrazolone and the 1,4-dihydro-2,6-dimethyl-4-(3-nitrophenyl)pyridine-3,5-dicarboxylic acid 3-ethyl ester 5-(6-tosyloxyhexyl) ester were replaced by the corresponding compounds, and further the sodium hydride or other aninoizing reagents or the solvent was appropriately chosen and used, to obtain the compounds in Examples 15–38 below.

EXAMPLE 15

1,4-Dihydro-2,6-dimethyl-4-(3-nitrophenyl)pyridine-3,5-dicarboxylic acid 3-ethyl ester 5-[6-(5-normalbutyl-3-pyrazolyloxy)hexyl]ester Aspect: Pale yellow powder.

IR Spectrum (CHCl$_3$) cm$^{-1}$: 3490, 3460, 2940, 1690, 1525.

PMR Spectrum (CDCl$_3$)δ: 0.68–1.11(3H), [1.22(3H,t) and 1.05–2.00(12H,m); total 15H], 2.30(6H,s), 2.30–2.75(2H), 3.83–4.21(6H,m), 5.01(1H,s), 5.35(1H,s), 6.80(1H,s), 7.05–8.10(4H,m), 8.92(1H,broad).

Analysis for $C_{30}H_{40}N_4O_7$: Calcd. (%): C,63.36; H,7.09; N,9.85. Found (%): C,63.81; H,7.48; N,9.71.

EXAMPLE 16

(Compound 8)

1,4-Dihydro-2,6-dimethyl-4-(3-nitrophenyl)pyridine-3,5-dicarboxylic acid 3-isopropyl ester 5-[6-(5-isopropyl-3-pyrazolyloxy)hexyl]ester Aspect: Pale yellow powder.

IR Spectrum (CHCl$_3$) cm$^{-1}$: 3490, 3465, 2940, 1690, 1520.

PMR Spectrum (CDCl$_3$+D$_2$O)δ: 0.91–1.86(20H,m), 2.30(6H,s), 2.53–3.13(1H,m), 3.80–4.17(4H,m), [4.63–5.10(1H,m) and 5.00(1H,s); total 2H], 5.38(1H,s), 7.13–8.07(4H,m).

Analysis for $C_{30}H_{40}N_4O_7$: Calcd. (%): C,63.36; H,7.09; N,9.85. Found (%): C,63.45; H,7.28; N,9.98.

EXAMPLE 17

1,4-Dihydro-2,6-dimethyl-4-(3-nitrophenyl)pyridine-3,5-dicarboxylic acid 3-isobutyl ester 5-[6-(5-methyl-3-pyrazolyloxy)hexyl]ester Aspect: Pale yellow powder.

IR Spectrum (CHCl$_3$) cm$^{-1}$: 3490, 3460, 2970, 2940, 1690, 1340.

PMR Spectrum (CDCl$_3$+D$_2$O)δ: 0.77(6H,dd), 1.00–2.07(9H,m), 2.12(3H,s), 2.23(6H,s), [3.70(2H,d) and 3.70–4.13(4H); total 6H], 5.02(1H,s), 5.32(1H,s), 7.00–8.06(4H,m).

Analysis for $C_{29}H_{38}N_4O_7$: Calcd. (%): C,62.80; H,6.91; N,10.10. Found (%): C,63.15; H,7.26; N,10.41.

EXAMPLE 18

(Compound 9)

1,4-Dihydro-2,6-dimethyl-4-(3-nitrophenyl)pyridine-3,5-dicarboxylic acid 3-isobutyl ester 5-[6-(5-ethyl-3-pyrazoloxy)hexyl]ester Aspect: Pale yellow powder.

IR Spectrum (CHCl$_3$) cm$^{-1}$: 3490, 3465, 2940, 1695, 1520, 1340, 1220, 1120.

PMR Spectrum (CDCl$_3$+D$_2$O)δ: 0.78(6H,dd), [1.20(3H,t) and 1.00–2.09(9H,m); total 12H], 2.30(6H,s), 2.53(2H,q), [3.70(2H,d) and 3.52–4.14(4H, m); total 6H], 5.00(1H,s), 5.30(1H,s), 7.00–8.10(4H,m).

Analysis for $C_{30}H_{40}N_4O_7$: Calcd. (%): C,63.36; H,7.09; N,9.85. Found (%): C,63.54; H,7.23; N,9.68.

EXAMPLE 19

1,4-Dihydro-2,6-dimethyl-4-(3-nitrophenyl)pyridine-3,5-dicarboxylic acid 3-(2-methoxyethyl) ester 5-[6-(5-normalbutyl-3-pyrazolyloxy)hexyl]ester Aspect: Pale yellow powder.

IR Spectrum (CHCl$_3$) cm$^{-1}$: 3495, 3460, 2940, 1690, 1525, 1340, 1220.

PMR Spectrum (CDCl$_3$+D$_2$O) δ: 0.67–1.08(3H), 1.08–2.00(12H,m), 2.33(6H,s), 2.53(2H,t), 3.30(3H,s), 3.52(2H,t), 3.76–4.32(6H,m), 5.07(1H,s), 5.40(1H,s), 7.05–8.10(4H,m).

Analysis for $C_{31}H_{42}N_4O_8$: Calcd. (%): C,62.19; H,7.07; N,9.36. Found (%): C,62.54; H,7.38; N,9.02.

EXAMPLE 20

1,4-Dihydro-2,6-dimethyl-4-(3-nitrophenyl)pyridine-3,5-dicarboxylic acid 3-(2-methoxyethyl) ester 5-[6-(5-isopropyl-3-pyrazolyloxy)hexyl]ester Aspect: Pale yellow powder.

IR Spectrum (CHCl$_3$) cm$^{-1}$: 3490, 3460, 2940, 1690, 1520, 1340.

PMR Spectrum (CDCl$_3$+D$_2$O) δ: [0.83–2.00(8H,m) and 1.23(6H,d); total 14H], 2.33(6H,s), 2.50–3.13(1H,m), 3.30(3H,s), 3.51(2H,t), 3.70–4.27(6H,m), 5.07(1H,s), 5.43(1H,s), 7.10–8.13(4H,m).

Analysis for $C_{30}H_{40}N_4O_8$: Calcd. (%): C,61.63; H,6.90; N,9.58. Found (%): C,61.99; H,7.38; N,9.25.

EXAMPLE 21

(Compound 10)

1,4-Dihydro-2,6-dimethyl-4-(3-nitrophenyl)pyridine-3,5-dicarboxylic acid 3-(2-normalpropoxyethyl) ester 5-[6-(5-ethyl-3-pyrazolyloxy)hexyl]ester Aspect: Pale yellow powder.

IR Spectrum (CHCl$_3$) cm$^{-1}$: 3495, 3460, 1687, 1458, 1342.

PMR Spectrum (CDCl$_3$) δ: 0.86(3H,t), [1.20(3H,t) and 1.00–1.90(10H,m); total 13H], 2.30(6H,s), 2.57(2H,q), 3.21–3.73(4H,m), 3.73–4.29(6H,m), 5.07(1H,s), 5.40(1H,s), 6.80(1H,s).

Analysis for $C_{31}H_{42}N_4O_8$: Calcd. (%): C,62.19; H,7.07; N,9.36. Found (%): C,62.28; H,7.16; N,9.50.

EXAMPLE 22

1,4-Dihydro-2,6-dimethyl-4-(3-nitrophenyl)pyridine-3,5-dicarboxylic acid 3-(2-normalpropoxyethyl) ester 5-[6-(5-isopropyl-3-pyrazolyloxy)hexyl]ester Aspect: Pale yellow powder.

IR Spectrum (CHCl$_3$) cm$^{-1}$: 3490, 3460, 1690, 1460, 1340.

PMR Spectrum (CDCl$_3$) δ: 0.86(3H,t), [1.20(6H,d) and 1.00–1.90(10H,m); total 16H], 2.30(6H,s), 2.55–3.05(1H,m), 3.20–3.73(4H,m), 3.73–4.30(6H,m), 5.05(1H,s), 5.38(1H,s), 6.75(1H,s).

Analysis for $C_{32}H_{44}N_4O_8$: Calcd. (%): C,62.73; H,7.24; N,9.14. Found (%): C,63.14; H,7.65; N,9.38.

EXAMPLE 23

(Compound 11)

1,4-Dihydro-2,6-dimethyl-4-(3-nitrophenyl)pyridine-3,5-dicarboxylic acid 3-(2-isobutoxyethyl) ester 5-[6-(5-methyl-3-pyrazolyloxy)hexyl]ester Aspect: Pale yellow powder.
IR Spectrum (CHCl$_3$) cm$^{-1}$: 3490, 3460, 3000, 2950, 2860, 1690, 1515.
PMR Spectrum (CDCl$_3$) δ: 0.87(6H,d), 1.13–2.00(9H,m), 2.19(3H,s), 2.33(6H,s), 3.15(2H,d), 3.36–3.73(2H), 3.83–4.26(6H,m), 5.03(1H,s), 5.36(1H,s).
Analysis for C$_{31}$H$_{42}$N$_4$O$_8$: Calcd. (%): C,62.19; H,7.07; N,9.36. Found (%): C,62.33; H,7.31; N,9.55.

EXAMPLE 24

1,4-Dihydro-2,6-dimethyl-4-(2-nitrophenyl)pyridine-3,5-dicarboxylic acid 3-(2-methoxyethyl) ester 5-[6-(5-methyl-3-pyrazolyloxy)-2,5-dimethylhexyl]ester Aspect: Pale yellow powder.
IR Spectrum (CHCl$_3$) cm$^{-1}$ 3490, 3455, 1685, 1515, 1345.
PMR Spectrum (CDCl$_3$) δ: 0.55–1.95(12H,m), 2.04–2.41(9H), 3.32(3H,s), 3.50(2H,t), 3.82–4.20(6H,m), 5.38(1H,s), 5.70(1H,s).
Analysis for C$_{30}$H$_{40}$N$_4$O$_8$: Calcd. (%): C,61.63; H,6.90; N,9.58. Found (%): C,61.92; H,7.34; N,9.77.

EXAMPLE 25

1,4-Dihydro-2,6-dimethyl-4-(2-nitrophenyl)pyridine-3,5-dicarboxylic acid 3-methyl ester 5-[6-(5-ethyl-3-pyrazolyloxy)-1,6-dimethylhexyl]ester Aspect: Pale yellow powder.
IR Spectrum (CHCl$_3$) cm$^{-1}$: 3490, 3455, 1680, 1520, 1345.
PMR Spectrum (CDCl$_3$) δ: 0.85–1.90(17H,m), 2.23(3H,s), 2.30(3H,s), 2.56(2H,q), 3.57(3H,s), 5.40(1H,s), 5.73(1H, s).
Analysis for C$_{29}$H$_{38}$N$_4$O$_7$: Calcd. (%): C,62.80; H,6.91; N,10.10. Found (%): C,62.98 H,7.05 N,10.40.

EXAMPLE 26

1,4-Dihydro-2,6-dimethyl-4-(2-nitrophenyl)pyridine-3,5-dicarboxylic acid 3-methyl ester 5-[6-(5-isopropyl-3-pyrazolyloxy)hexyl]ester Aspect: Pale yellow powder.
IR Spectrum (CHCl$_3$) cm$^{-1}$: 3490, 3460, 1685, 1520, 1340.
PMR Spectrum (CDCl$_3$) δ: [1.00–1.90(8H,m) and 1.20(6H,d); total 14H], 2.21(3H,s), 2.27(3H,s), 2.55–3.00(1H,m), 3.55(3H,s), 3.76–4.15(4H), 5.38(1H,s), 5.72(1H,s).
Analysis for C$_{28}$H$_{36}$N$_4$O$_7$: Calcd. (%): C,62.21; H,6.71; N,10.36. Found (%): C,62.60; H,6.98; N,10.75.

EXAMPLE 27

1,4-Dihydro-2,6-dimethyl-4-(2-nitrophenyl)pyridine-3,5-dicarboxylic acid 3-ethyl ester 5-[6-(5-methyl-3-pyrazolyloxy)-2,5-diisopropylhexyl]ester Aspect: Pale yellow powder.
IR Spectrum (CHCl$_3$) cm$^{-1}$: 3490, 3460, 1685, 1520, 1345.
PMR Spectrum (CDCl$_3$) δ: 0.57–2.00(23H,m), 2.04–2.50(9H), 3.78–4.22(6H,m), 5.37(1H,s), 5.70(1H,s).
Analysis for C$_{33}$H$_{46}$N$_4$O$_7$: Calcd. (%): C,64.89; H,7.59; H,9.17. Found (%): C,65.26; H,7.95; H,9.01.

EXAMPLE 28

(Compound 12)

1,4-Dihydro-2,6-dimethyl-4-(2-nitrophenyl)pyridine-3,5-dicarboxylic acid 3-isopropyl ester 5-[6-(5-normalbutyl-3-pyrazolyloxy)hexyl]ester Aspect: Pale yellow powder.
IR Spectrum (CHCl$_3$) cm$^{-1}$: 3490, 3455, 1685, 1345.
PMR Spectrum (CDCl$_3$) δ: 2.20(3H,s), 2.25(3H,s), 2.30–2.70(2H), 3.80–4.20(6H,m), 4.55–5.05(1H,m), 5.40(1H,s), 5.70(1H,s).
Analysis for C$_{31}$H$_{42}$N$_4$O$_7$: Calcd. (%): C,63.90; H,7.27; N,9.62. Found (%): C,63.99; H,7.46; N,9.68.

EXAMPLE 29

1,4-Dihydro-2,6-dimethyl-4-(2-nitrophenyl)pyridine-3,5-dicarboxylic acid 3-methyl ester 5-[6-(5-methyl-3-pyrazolyloxy)-1,6-diethylhexyl]ester Aspect: Pale yellow powder.
IR Spectrum (CHCl$_3$) cm$^{-1}$: 3485, 1685, 1520.
PMR Spectrum (CDCl$_3$) δ: 0.58–1.95(18H,m), 2.04–2.40(9H,m), 3.60(3H,s), 5.40(1H,s), 5.70(1H,s).
Analysis for C$_{30}$H$_{40}$N$_4$O$_7$: Calcd. (%): C,63.36; H,7.09; N,9.85. Found (%): C,63.75; H,7.42; N,9.98.

EXAMPLE 30

1,4-Dihydro-2,6-dimethyl-4-(3-nitrophenyl)pyridine-3,5-dicarboxylic acid 3-ethyl ester 5-[6-(5-isopropyl-3-pyrazolyloxy)-1,6-dimethylhexyl]ester Aspect: Pale yellow powder.
IR Spectrum (CHCl$_3$) cm$^{-1}$: 3490, 3460, 1690, 1520, 1342.
PMR SPectrum (CDCl$_3$) δ: 0.65–2.00(23H,m), 2.30(6H,s), 2.56–3.00(1H,m), 4.00(2H,t), 5.10(1H,s), 5.40(1H,s).
Analysis for C$_{31}$H$_{42}$N$_4$O$_7$: Calcd. (%): C,63.90; H,7.27; N,9.62. Found (%): C,64.35; H,7.65; N,9.91.

EXAMPLE 31

1,4-Dihydro-2,6-dimethyl-4-(2-nitrophenyl)pyridine-3,5-dicarboxylic acid 3-(2-methoxyethyl) ester 5-[6-(5-ethyl-3-pyrazolyloxy)hexyl]ester Aspect: Pale yellow powder.
IR Spectrum (CHCl$_3$) cm$^{-1}$: 3485, 3455, 1685, 1220.
PMR Spectrum (CDCl$_3$) δ: 3.32(3H,s), 3.50(2H,t), 3.70–4.32(6H,m), 5.40(1H,s), 5.70(1H,s).
Analysis for C$_{29}$H$_{38}$N$_4$O$_8$: Calcd. (%): C,61.04; H,6.71; N,9.82. Found (%): C,61.35; H,6.40; N,9.53.

EXAMPLE 32

1,4-Dihydro-2,6-dimethyl-4-(3-nitrophenyl)pyridine-3,5-dicarboxylic acid 3-ethyl ester 5-[6-(5-ethyl-3-pyrazolyloxy)hexyl]ester Aspect: Pale yellow powder.
IR Spectrum (CHCl$_3$) cm$^{-1}$: 3490, 3460, 2940, 1695, 1520, 1340.
PMR Spectrum (CDCl$_3$) δ: 2.33(6H,s), 2.56(2H,q), 3.80–4.25(6H,m), 5.00(1H,s), 5.40(1H,s), 6.71(1H,s).
Analysis for C$_{28}$H$_{36}$N$_4$O$_7$: Calcd. (%): C,62.21; H,6.71; N,10.36. Found (%): C,62.60; H,6.33; N,10.12.

EXAMPLE 33

(Compound 13)

1,4-Dihydro-2,6-dimethyl-4-(3-nitrophenyl)pyridine-3,5-dicarboxylic acid 3-methyl ester 5-[6-(5-normalbutyl-3-pyrazolyloxy)hexyl]ester Aspect: Pale yellow powder.

IR Spectrum (CHCl$_3$) cm$^{-1}$: 3490, 3460, 2940, 1690, 1520, 1340, 1220.

PMR Spectrum (CDCl$_3$+D$_2$O) δ: 0.70–1.10(3H), 1.10–2.00(12H,m), 2.30(6H,s), 2.30–2.70(2H), 3.57(3H,s), 3.70–4.17(4H), 5.00(1H,s), 5.34(1H,s), 7.02–8.10(4H,m).

Analysis for C$_{29}$H$_{38}$N$_4$O$_7$: Calcd. (%): C,62.80; H,6.91; N,10.10. Found (%): C,62.97; H,6.76; N,10.21.

EXAMPLE 34

1,4-Dihydro-2,6-dimethyl-4-(3-nitrophenyl)pyridine-3,5-dicarboxylic acid 3-normalpropyl ester 5-[6-(5-ethyl-3-pyrazolyloxy)hexyl]ester Aspect: Pale yellow powder.

IR Spectrum (CHCl$_3$) cm$^{-1}$: 3490, 3460, 2940, 1690.

PMR Spectrum (CDCl$_3$) δ: 2.30(6H,s), 2.55(2H), 3.83–4.22(6H,m), 5.00(1H,s), 5.35(1H,s), 6.64(1H,s).

Analysis for C$_{29}$H$_{38}$N$_4$O$_7$: Calcd. (%): C,62.80; H,6.91; N,10.10. Found (%): C,63.14; H,6.76; N,10.41.

EXAMPLE 35

(Compound 14)

1,4-Dihydro-2,6-dimethyl-4-(3-nitrophenyl)pyridine-3,5-dicarboxylic acid 3-normalpropyl ester 5-[6-(5-isopropyl-3-pyrazolyloxy)hexyl]ester Aspect: Pale yellow powder.

IR Spectrum (CHCl$_3$) cm$^{-1}$: 3490, 3465, 2940, 1690, 1520.

PMR Spectrum (CDCl$_3$) δ: 2.30(6H,s), 2.50–3.00(1H,m), 3.83–4.25(6H,m), 5.01(1H,s), 5.40(1H,s), 6.81(1H,s).

Analysis for C$_{30}$H$_{40}$N$_4$O$_7$: Calcd. (%): C,63.36; H,7.09; N,9.85. Found (%): C,63.47; H,7.18; N,9.68.

EXAMPLE 36

1,4-Dihydro-2,6-dimethyl-4-(2-nitrophenyl)pyridine-3,5-dicarboxylic acid 3-ethyl ester 5-[6-(5-ethyl-3-pyrazolyloxy)hexyl]ester Aspect: Pale yellow powder.

IR Spectrum (CHCl$_3$) cm$^{-1}$: 3490, 3455, 1685.

PMR Spectrum (CDCl$_3$) δ: 2.20(3H,s), 2.27(3H,s), 2.56(2H,q), 3.80–4.20(6H,m), 5.40(1H,s), 5.70(1H,s).

Analysis for C$_{28}$H$_{36}$N$_4$O$_7$: Calcd. (%): C,62.21; H,6.71; N,10.36. Found (%): C,62.46; H,6.44; N,10.75.

EXAMPLE 37

(Compound 15)

1,4-Dihydro-2,6-dimethyl-4-(2-nitrophenyl)pyridine-3,5-dicarboxylic acid 3-methyl ester 5-[6-(5-octyl-3-pyrazolyloxy)hexyl]ester Aspect: Pale yellow powder.

IR Spectrum (CHCl$_3$) cm$^{-1}$: 3485, 3455, 1690.

PMR Spectrum (CDCl$_3$) δ: 0.57–2.00(23H,m), 2.21(3H,s), 2.28(3H,s), 2.30–2.70(2H), 3.56(3H,s), 3.76–4.16(4H,m), 5.40(1H,s), 5.70(1H,s).

Analysis for C$_{33}$H$_{46}$N$_4$O$_7$: Calcd. (%): C,64.90; H,7.59; N,9.17. Found (%): C,64.78; H,7.71; N,9.36.

EXAMPLE 38

1,4-Dihydro-2,6-dimethyl-4-(3-nitrophenyl)pyridine-3,5-dicarboxylic acid 3-methyl ester 5-[6-(5-methyl-3-pyrazolyloxy)-5,5-dimethylhexyl]ester Aspect: Pale yellow powder.

IR Spectrum (CHCl$_3$) cm$^{-1}$: 3490, 3460, 1690, 1520.

PMR Spectrum (CDCl$_3$) δ: 0.64–1.95(12H,m), 2.20(3H,s), 2.30(6H,s), 3.60(3H,s), 3.80–4.23(4H,m), 5.10(1H,s), 5.40(1H,s).

Analysis for C$_{28}$H$_{36}$N$_4$O$_7$: Calcd. (%): C,62.21; H,6.71; N,10.36. Found (%): C,62.58; H,6.99; N,10.15.

EXAMPLE 39

(Compound 16)

0.72 g (30 mmole) of sodium hydride was suspended in 60 ml of N,N-dimethylformamide, to which was added gradually 5.60 g (50 mmole) of 3-ethyl-5-pyrazolone with stirring at room temperature, and the mixture was allowed to stand until evolution of hydrogen ceased. To this solution was added dropwise 40 ml of a solution of 4.91 g (10 mmole) of 1,4-dihydro-2,6-dimethyl-4-(3-nitrophenyl)pyridine-3,5-dicarboxylic acid 3-methyl ester 5-(6-chlorohexyl) ester in N,N-dimethylformamide, the mixture was heated at 90°–100° C. for 3 hours and then allowed to stand at room temperature. After cooling, the reaction mixture was poured into 400 ml of ice water, the resulting separated product was extracted with 100 ml of ethyl acetate, and this was washed with water, dried, and concentrated under reduced pressure to obtain a brown oily residual liquid. This residual liquid was purified by subjecting to silica gel column chromatography using a mixed solution of chloroform-ethanol (the ratio by volume of 20:1) as an eluent to obtain 1.79 g (yield 34.0%) of a pale yellow powder of the 1,4-dihydro-2,6-dimethyl-4-(3-nitrophenyl)pyridine-3,5-dicarboxylic acid 3-methyl ester 5-[6-(5-ethyl-3-pyrazolyloxy)hexyl]ester.

IR Spectrum (CHCl$_3$) cm$^{-1}$: 3490, 3465, 2940, 1690, 1520.

PMR Spectrum (CDCl$_3$+D$_2$O ) δ: [1.20(3H,t), 1.00–1.89(8H,m); total 11H], 2.33(6H,s), 2.56(2H,q), 3.60(3H,s), 4.00(4H,t), 5.05(1H,s), 5.40(1H,s), 7.07–8.08(4H,m).

Analysis for C$_{27}$H$_{34}$N$_4$O$_7$: Calcd. (%): C,61.58; H,6.51; N,10.64. Found (%): C,61.74; H,6.80; N,10.42.

Procedures similar to the above were repeated, except that the 3-ethyl-5-pyrazolone and the 1,4-dihydro-2,6-dimethyl-4-(3-nitrophenyl)pyridine-3,5-dicarboxylic acid 3-methyl ester 5-(6-chlorohexyl) ester were replaced by the corresponding compounds, and further the sodium hydride or other anionizing reagents or the solvent was appropriately chosen and used, to obtain the compounds in Examples 40–47 below.

EXAMPLE 40

(Compound 17)

1,4-Dihydro-2,6-dimethyl-4-(3-nitrophenyl)pyridine-3,5-dicarboxylic acid 3-methyl ester 5-[6-(5-methyl-3-pyrazolyloxy)-1-methylhexyl]ester Aspect: Pale yellow powder.

IR Spectrum (CHCl$_3$) cm$^{-1}$: 3490, 3460, 1690, 1520.

PMR Spectrum (CDCl$_3$) δ: 0.92–1.95(11H,m), 2.20(3H,s), 2.27(6H,s), 3.60(3H,s), 3.80–4.18(2H,t), 4.60–5.06(1H,m), 5.09(1H,s), 5.38(1H,s).

Analysis for $C_{27}H_{34}N_4O_7$: Calcd. (%): C,61.58; H,6.51; N,10.64. Found (%): C,61.71; H,6.79; N,10.85.

EXAMPLE 41

1,4-Dihydro-2,6-dimethyl-4-(3-nitropheyl)pyridine-3,5-dicarboxylic acid 3-methyl ester 5-[6-(5-iso propyl-3-pyrazolyloxy)-1-methylhexyl]ester Aspect: Pale yellow powder.

IR Spectrum ($CHCl_3$) $cm^{-1}$: 3490, 3460, 2940, 1690, 1520.

PMR Spectrum ($CDCl_3$) δ: 0.95–1.95(17H,m), 2.30(6H,s), 2.55–3.00(1H,m), 3.57(3H,s), 3.75–4.23(2H), 4.50–5.16(1H,m), 5.38(1H,s), 5.69(1H,s).

Analysis for $C_{29}H_{38}N_4O_7$: Calcd. (%): C,62.80; H,6.91; N,10.10. Found (%): C,62.99; H,7.30; N,10.39.

EXAMPLE 42

(Compound 18)

1,4-Dihydro-2,6-dimethyl-4-(3-nitrophenyl)pyridine-3,5-dicarboxylic acid 3-methyl ester 5-[6-(5-hexyl-3-pyrazolyloxy)hexyl]ester Aspect: Pale yellow powder.

IR Spectrum ($CHCl_3$) $cm^{-1}$: 3490, 3460, 1690, 1340, 1220.

PMR Spectrum ($CDCl_3 + D_2O$) δ: 0.55–2.00(19H,m), 2.30(6H,s), 2.30–2.70(2H), 3.56(3H,s), 3.73–4.21(4H), 5.04(1H,s), 5.38(1H,s), 7.02–8.09(4H,m).

Analysis for $C_{31}H_{42}N_4O_7$: Calcd. (%): C,63.90; H,7.27; N,9.62. Found (%): C,63.81; H,7.48; N,9.83.

EXAMPLE 43

1,4-Dihydro-2,6-dimethyl-4-(2-nitrophenyl)pyridine-3,5-dicarboxylic acid 3-ethyl ester 5-[6-(5-ethyl-3-pyrazolyloxy)-5-methylhexyl]ester Aspect: Pale yellow powder.

IR Spectrum ($CHCl_3$) $cm^{-1}$: 3490, 3455, 1690.

PMR Spectrum ($CDCl_3 + D_2O$) δ: 0.66–1.95(16H, m), 2.21(3H,s), 2.28(3H,s), 2.56(2H,q), 3.83–4.20(6H,m), 5.40(1H,s), 5.70(1H,s), 6.93–7.70(4H,m).

Analysis for $C_{29}H_{38}N_4O_7$: Calcd. (%): C,62.80; H,6.91 N,10.10. Found (%): C,63.20; H,7.25 N,10.03.

EXAMPLE 44

1,4-Dihydro-2,6-dimethyl-4-(3-nitrophenyl)pyridine-3,5-dicarboxylic acid 3-normalpropyl ester 5-[6-(5-methyl-3-pyrazolyloxy)hexyl]ester Aspect: Pale yellow powder.

IR Spectrum ($CHCl_3$) $cm^{-1}$: 3490, 3465, 2940, 1695, 1520.

PMR Spectrum ($CDCl_3$) δ: 0.90(3H,t), 1.00–2.00(10H,m), 2.18(3H,s), 2.30(6H,s), 3.80–4.25(6H,m), 5.00(1H,s), 5.40(1H,s).

Analysis for $C_{28}H_{36}N_4O_7$: Calcd. (%): C,62.21; H,6.71; N,10.36. Found (%): C,62.52; H,6.98; N,10.21.

EXAMPLE 45

1,4-Dihydro-2,6-dimethyl-4-(3-nitrophenyl)pyridine-3,5-dicarboxylic acid 3-isopropyl ester 5-[6-(5-ethyl-3-pyrazolyloxy)hexyl]ester Aspect: Pale yellow powder.

IR Spectrum ($CHCl_3$) $cm^{-1}$: 3490, 3465, 2940, 1695, 1520.

PMR Spectrum ($CDCl_3$) δ: 1.00–2.00(17H,m), 2.33(6H,s), 2.56(2H,q), 3.80–4.15(4H,), 4.60–5.00(1H,m), 5.03(1H,s), 5.40(1H,s), 6.30(1H,s).

Analysis for $C_{29}H_{38}N_4O_7$: Calcd. (%): C,62.80; H,6.91; N,10.10. Found (%): C,62.98; H,7.05; N,10.45.

EXAMPLE 46

1,4-Dihydro-2,6-dimethyl-4-(3-nitrophenyl)pyridine-3,5-dicarboxylic acid 3-(2-methoxyethyl) ester 5-[6-(5-ethyl-3-pyrazolyloxy)hexyl]ester Aspect: Pale yellow powder.

IR Spectrum ($CHCl_3$) $cm^{-1}$ 3490, 3460, 2940, 1690, 1340.

PMR Spectrum ($CDCl_3$) δ: 1.20(3H,t), 1.00–2.00(8H,m), 2.30(6H,s), 2.56(2H,q), 3.30(3H,s), 3.50(2H,t), 3.73–4.25(6H,m), 5.04(1H,s), 5.40(1H,s), 6.80(1H,s).

Analysis for $C_{29}H_{38}N_4O_8$: Calcd. (%): C,61.04; H,6.71; N,9.82. Found (%): C,61.43; H,6.98; N,9.61.

EXAMPLE 47

(Compound 19)

1,4-Dihydro-2,6-dimethyl-4-(3-nitrophenyl)pyridine-3,5-dicarboxylic acid 3-(2-isopropoxyethyl) ester 5-[6-(5-methyl-3-pyrazolyloxy)hexyl]ester Aspect: Pale yellow powder.

IR Spectrum ($CHCl_3$) $cm^{-1}$: 3495, 3460, 1690, 1520, 1455.

PMR Spectrum ($CDCl_3$) δ: 1.13(6H,d), 0.83–2.00(8H,m), 2.18(3H,s), 2.30(6H,s), 3.23–4.50(9H,m), 5.09(1H,s), 5.37(1H,s).

Analysis for $C_{30}H_{40}N_4O_8$: Calcd. (%): C,61.63; H,6.90; N,9.58. Found (%): C,61.85; H,6.77; N,9.61.

EXAMPLE 48

To 15 ml of a suspension of 0.36 g (15 mmole) of sodium hydride in N,N-dimethylformamide was added gradually 2.00 g (20 mmole) of 3-methyl-5-pyrazolone with stirring at room temperature, and the mixture was allowed to stand until evolution of hydrogen ceased. To this solution was added dropwise a solution of 5.87 g (10 mmole) of 1,4-dihydro-2,6-dimethyl-4-(3-nitrophenyl)-pyridine-3,5-dicarboxylic acid 3-methyl ester 5-(6-tosyloxyhexyl) ester dissolved in 15 ml of N,N-dimethylformamide. After completion of the addition, the mixture was stirred at 100° C. for an hour, the reaction mixture was poured into 200 ml of ice water, and extracted with 100 ml of ethyl acetate. The ethyl acetate extract was washed with water, dried and then concentrated under reduced pressure before subjecting to silica gel column chromatography. The substances adsorbed onto the fixed phase were monitored by thin layer chromatography and carefully eluted using a mixed solution of benzene-ethyl acetate (the ratio by volume of 1:1), to obtain two kinds of eluted fractions, each containing a single substance different from each other. The first eluted fraction was concentrated to dryness under reduced pressure to obtain 2.95 g (yield 57.5%) of a pale yellow powder of 1,4-dihydro-2,6-dimethyl-4-(3-nitrophenyl)pyridine-3,5-dicarboxylic acid 3-methyl ester 5-[6-(5-methyl-3-pyrazolyloxy)hexyl]ester.

Analysis for $C_{26}H_{32}N_4O_7$: Calcd. (%): C,60.93; H,6.29; N,10.93. Found (%): C,61.20; H,6.41; N,10.69.

Both IR and PMR spectra agreed with those obtained in Example 1.

Thereafter, the later eluted fraction was concentrated to dryness under reduced pressure to obtain 0.49 g (yield 7.8%) of a pale yellow oil of 1,4-dihydro-2,6-dimethyl-4-(3-nitrophenyl)pyridine-3,5-dicarboxylic acid 3-methyl ester 5-[6-(3-hydroxy-5-methyl-1-pyrazolyl)hexyl]ester.

IR Spectrum (CHCl$_3$) cm$^{-1}$: 3460, 2490, 1690, 1520, 1340, 1220.

PMR Spectrum (CDCl$_3$+D$_2$O) δ: 1.00–1.90(8H,m), 2.13(3H,s), 3.60(3H,s), 3.73(2H,t), 3.96(2H,t), 5.00(1H,s), 5.17(1H,s), 7.00–8.10(4H,m).

Analysis for C$_{26}$H$_{32}$N$_4$O$_7$: Calcd. (%): C,60.93; H,6.29; N,10.93. Found (%): C,61.18; H,6.42; N,10.73.

What is claimed is:

1. A 1,4-dihydropyridine derivative of the following general formula [I]:

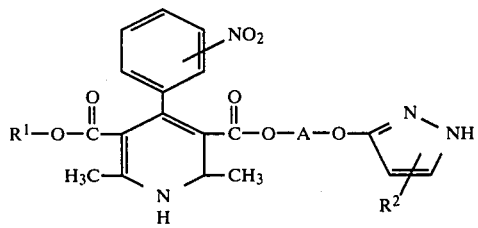

[I]

wherein R$^1$ represents an alkyl group having from 1 to 4 carbon atoms or an alkoxyalkyl group having from 3 to 6 carbon atoms, R$^2$ represents an alkyl group having from 1 to 8 carbon atoms, and A represents a hexamethylene group which may optionally be substituted by one or two alkyl groups having from 1 to 3 carbon atoms.

2. A 1,4-dihydropyridine derivative according to claim 1, wherein R$^1$ represents one member selected from the group consisting of methyl, ethyl, butyl, methoxyethyl and propoxymethyl, R$^2$ represents one member selected from the group consisting of methyl, ethyl, propyl, hexyl and octyl, and A represents hexamethylene.

3. 1,4-Dihydro-2,6-dimethyl-4-(3-nitrophenyl)pyridine-3,5-carboxylic acid 3-methyl ester 5-[6-(5-methyl-3-pyrazolyloxy)hexyl]ester.

4. 1,4-Dihydro-2,6-dimethyl-4-(3-nitrophenyl)pyridine-3,5-dicarboxylic acid 3-methyl ester 5-[6-(5-isopropyl-3-pyrazolyloxy)hexyl]ester.

5. 1,4-Dihydro-2,6-dimethyl-4-(3-nitrophenyl)pyridine-3,5-dicarboxylic acid 3-ethyl ester 5-[6-(5-methyl-3-pyrazolyloxy)hexyl]ester.

6. 1,4-Dihydro-2,6-dimethyl-4-(3-nitrophenyl)pyridine-3,5-dicarboxylic acid 3-(2-methoxyethyl) ester 5-[6-(5-methyl-3-pyrazolyloxy)hexyl]ester.

7. 1,4-Dihydro-2,6-dimethyl-4-(2-nitrophenyl)pyridine-3,5-dicarboxylic acid 3-methyl ester 5-[6-(5-methyl-3-pyrazolyloxy)hexyl]ester.

8. 1,4-Dihydro-2,6-dimethyl-4-(3-nitrophenyl)pyridine-3,5-dicarboxylic acid 3-isobutyl ester 5-[6-(5-ethyl-3-pyrazolyloxy)hexyl]ester.

9. 1,4-Dihydro-2,6-dimethyl-4-(3-nitrophenyl)pyridine-3,5-dicarboxylic acid 3-(2-normalpropoxyethyl) ester 5-[6-(5-ethyl-3-pyrazolyloxy)hexyl]ester.

10. 1,4-Dihydro-2,6-dimethyl-4-(2-nitrophenyl)pyridine-3,5-dicarboxylic acid 3-methyl ester 5-[6-(5-octyl-3-pyrazolyloxy)hexyl]ester.

11. 1,4-Dihydro-2,6-dimethyl-4-(3-nitrophenyl)pyridine-3,5-dicarboxylic acid 3-methyl ester 5-[6-(5-hexyl-3-pyrazolyloxy)hexyl]ester.

* * * * *